(12) United States Patent  
Reynolds et al.

(10) Patent No.: US 7,074,197 B2  
(45) Date of Patent: *Jul. 11, 2006

(54) COMPOSITE GUIDEWIRE

(75) Inventors: Brian Reynolds, Ramsey, MN (US); Peter Skujins, Minneapolis, MN (US); Brice Shireman, Maple Grove, MN (US); Bruce H. Asmus, Minnetonka, MN (US); Ron Tanaka, Bloomington, MN (US); Michael Swee, Maple Grove, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 161 days.

This patent is subject to a terminal disclaimer.

(21) Appl. No.: 10/086,992

(22) Filed: Feb. 28, 2002

(65) Prior Publication Data

US 2003/0069521 A1    Apr. 10, 2003

Related U.S. Application Data

(63) Continuation-in-part of application No. 09/972,276, filed on Oct. 5, 2001, now Pat. No. 6,918,882.

(51) Int. Cl.  
*A61B 5/00* (2006.01)  
*A61M 25/00* (2006.01)

(52) U.S. Cl. ...................... 600/585; 600/434

(58) Field of Classification Search ........ 600/433–435, 600/585; 604/164.13, 523, 524  
See application file for complete search history.

(56) References Cited

U.S. PATENT DOCUMENTS

| | | | |
|---|---|---|---|
| 4,080,706 A | 3/1978 | Heilman et al. | |
| 4,456,017 A | 6/1984 | Miles | |
| 4,538,622 A | 9/1985 | Samson et al. | |
| 4,556,240 A | 12/1985 | Yoshida | |
| 4,748,986 A * | 6/1988 | Morrison et al. | 600/585 |
| 4,763,647 A | 8/1988 | Gambale | |
| 4,813,434 A | 3/1989 | Buchbinder et al. | |
| 4,832,047 A * | 5/1989 | Sepetka et al. | 600/585 |
| 4,846,186 A | 7/1989 | Box et al. | |
| 4,884,579 A | 12/1989 | Engelson | |
| 4,925,445 A | 5/1990 | Sakamoto et al. | |
| 4,984,581 A | 1/1991 | Stice | |
| 5,069,226 A | 12/1991 | Yamauchi et al. | |
| 5,109,867 A | 5/1992 | Twyford, Jr. | |
| 5,111,829 A | 5/1992 | Alvarez de Toledo | |
| 5,144,959 A * | 9/1992 | Gambale et al. | 600/585 |
| 5,213,111 A | 5/1993 | Cook et al. | |

(Continued)

FOREIGN PATENT DOCUMENTS

EP    0 274 412    7/1988

(Continued)

OTHER PUBLICATIONS

Furukawa Techno Material Co., LTD, "Furukawa NT-Wires for Medical Guidewires," 2 pages, 2000. Article from website: http://www.fitec.co.jp/ftm/nt-e/fhp-nt.htm.

*Primary Examiner*—Charles Marmor

(57) ABSTRACT

Alternative designs, materials and manufacturing methods for guidewires. Some embodiments pertain to a composite guidewire having proximal and distal section, and a connector adapted and configured for permanently joining the proximal section to the distal section. In some embodiments, at least one of the sections is made of a linear-elastic nickel-titanium alloy. Several alternative guidewire tip designs including coiled safety/shaping structures are also disclosed.

39 Claims, 11 Drawing Sheets

U.S. PATENT DOCUMENTS

| | | |
|---|---|---|
| 5,238,004 A | 8/1993 | Sahatjian et al. |
| 5,273,052 A | 12/1993 | Kraus et al. |
| 5,275,173 A | 1/1994 | Samson et al. |
| 5,312,356 A | 5/1994 | Engelson et al. |
| 5,333,620 A | 8/1994 | Moutafis et al. |
| 5,341,818 A | 8/1994 | Abrams et al. |
| 5,365,943 A | 11/1994 | Jansen |
| 5,402,829 A | 4/1995 | Takikawa et al. |
| 5,411,476 A | 5/1995 | Abrams et al. |
| 5,433,200 A | 7/1995 | Fleischhacker, Jr. |
| 5,452,726 A | 9/1995 | Burmeister et al. |
| 5,637,089 A | 6/1997 | Abrams et al. |
| 5,651,373 A | 7/1997 | Mah |
| 5,695,111 A | 12/1997 | Nanis et al. |
| 5,772,641 A | 6/1998 | Wilson |
| 5,782,776 A | 7/1998 | Hani |
| 5,797,857 A | 8/1998 | Obitsu |
| 5,820,571 A | 10/1998 | Erades et al. |
| 5,833,631 A | 11/1998 | Nguyen |
| 5,836,893 A | 11/1998 | Urick |
| 5,980,471 A | 11/1999 | Jafari |
| 6,001,068 A | 12/1999 | Uchino et al. |
| 6,042,553 A | 3/2000 | Solar et al. |
| 6,106,488 A | 8/2000 | Fleming et al. |
| 6,165,292 A | 12/2000 | Abrams et al. |
| 6,168,571 B1 | 1/2001 | Solar et al. |
| 6,183,420 B1 | 2/2001 | Douk et al. |
| 6,234,981 B1 | 5/2001 | Howland |
| 6,248,082 B1 | 6/2001 | Jafari |
| 6,306,105 B1 | 10/2001 | Rooney et al. |
| 6,352,515 B1 | 3/2002 | Anderson et al. |
| 6,464,651 B1 | 10/2002 | Hiejima et al. |
| 6,488,637 B1 * | 12/2002 | Eder et al. .................. 600/585 |
| 6,497,709 B1 | 12/2002 | Health |
| 6,554,942 B1 | 4/2003 | Solar et al. |
| 6,561,218 B1 | 5/2003 | Mudd |
| 6,592,570 B1 * | 7/2003 | Abrams et al. ............. 604/525 |
| 6,610,046 B1 | 8/2003 | Usami et al. |
| 6,673,025 B1 * | 1/2004 | Richardson et al. ........ 600/585 |
| 6,682,493 B1 | 1/2004 | Mirigian |
| 2002/0019599 A1 * | 2/2002 | Rooney et al. ............. 600/585 |

FOREIGN PATENT DOCUMENTS

| | | |
|---|---|---|
| EP | 0 491 349 | 6/1992 |
| EP | 0 806 220 | 11/1997 |
| EP | 0 838 230 | 4/1998 |
| WO | WO 00/402860 | 7/2000 |

* cited by examiner

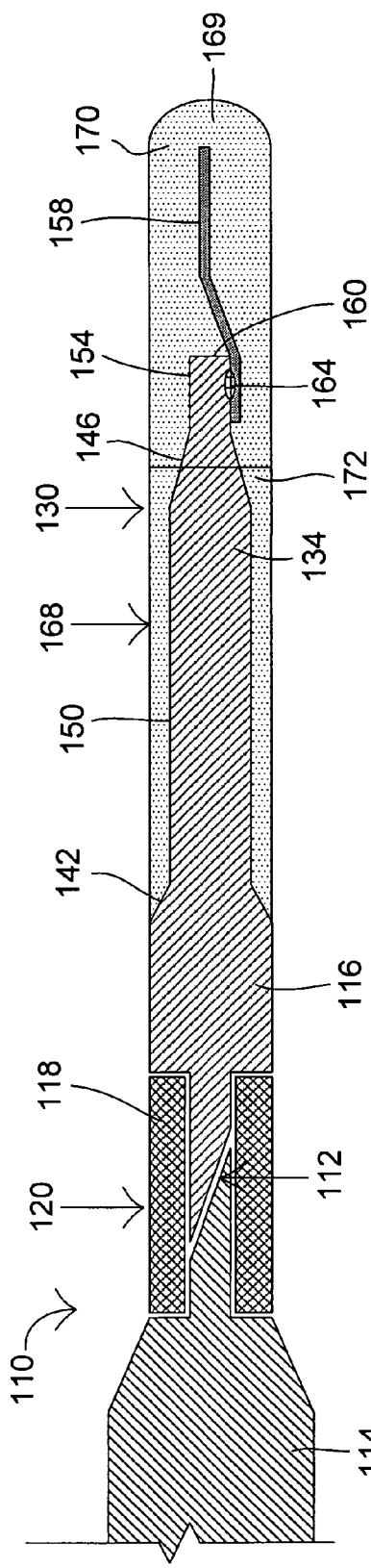
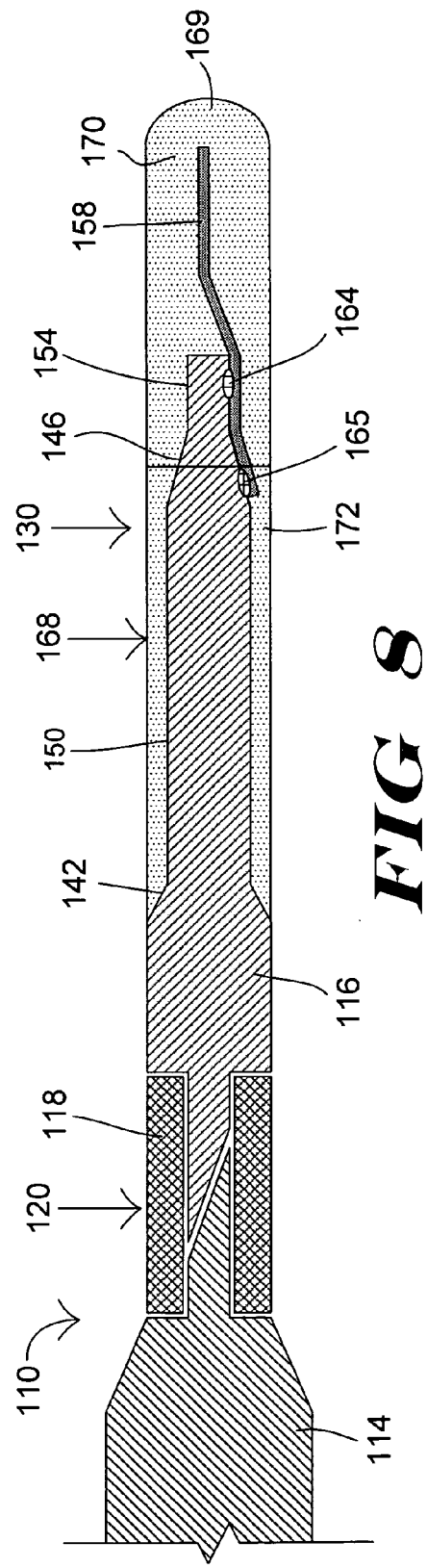

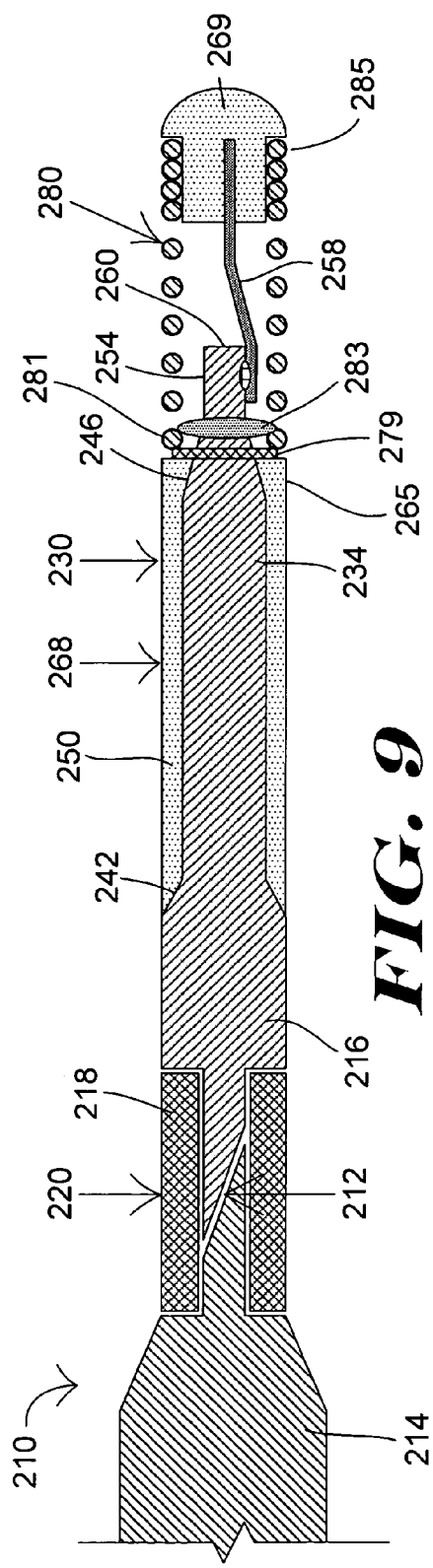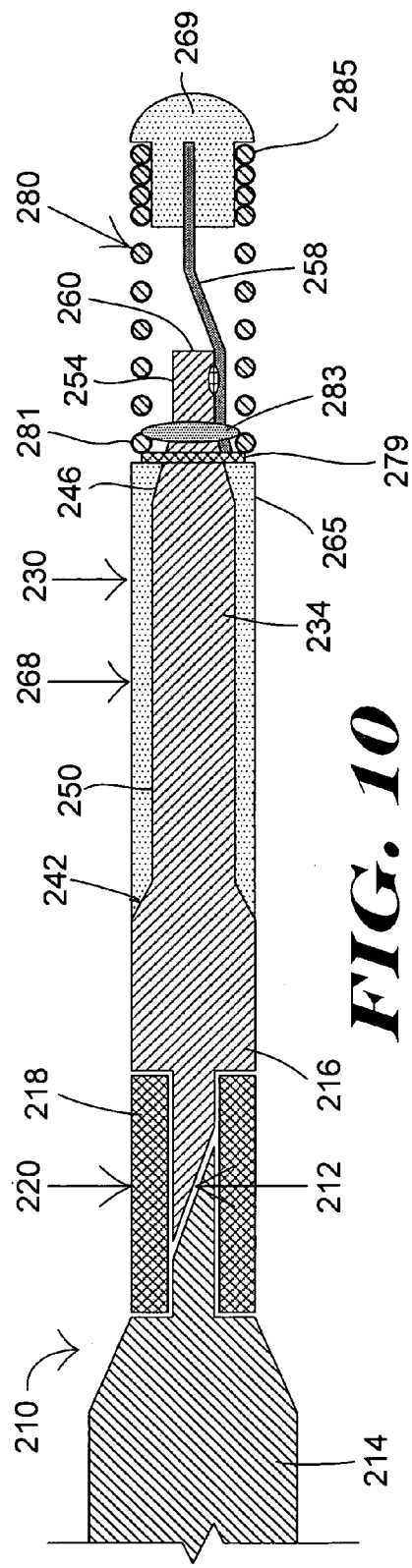

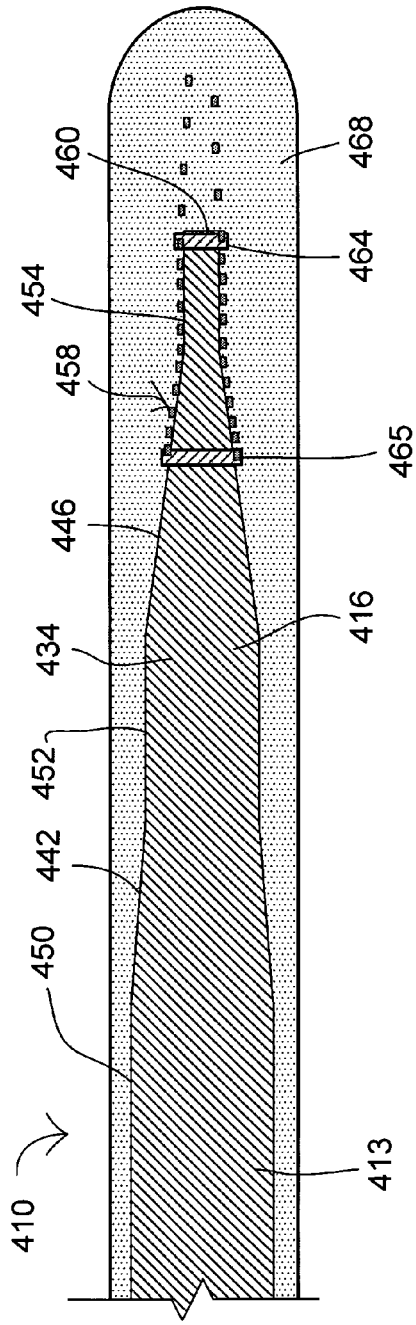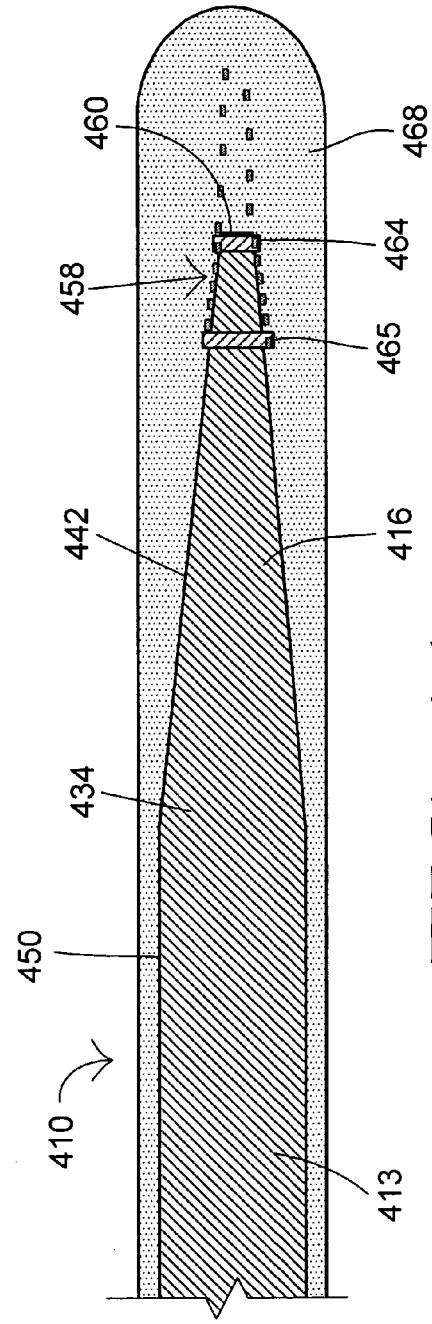
FIG. 13
FIG. 14

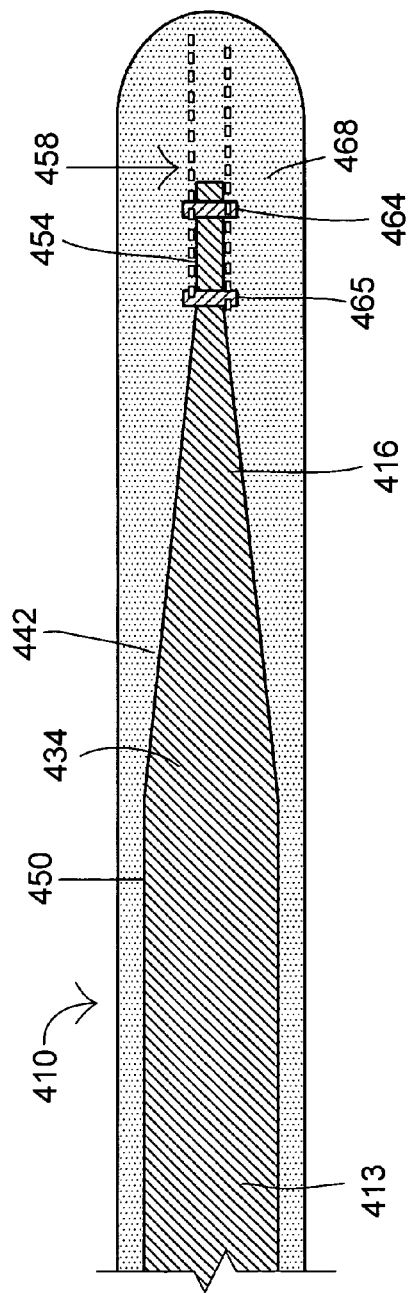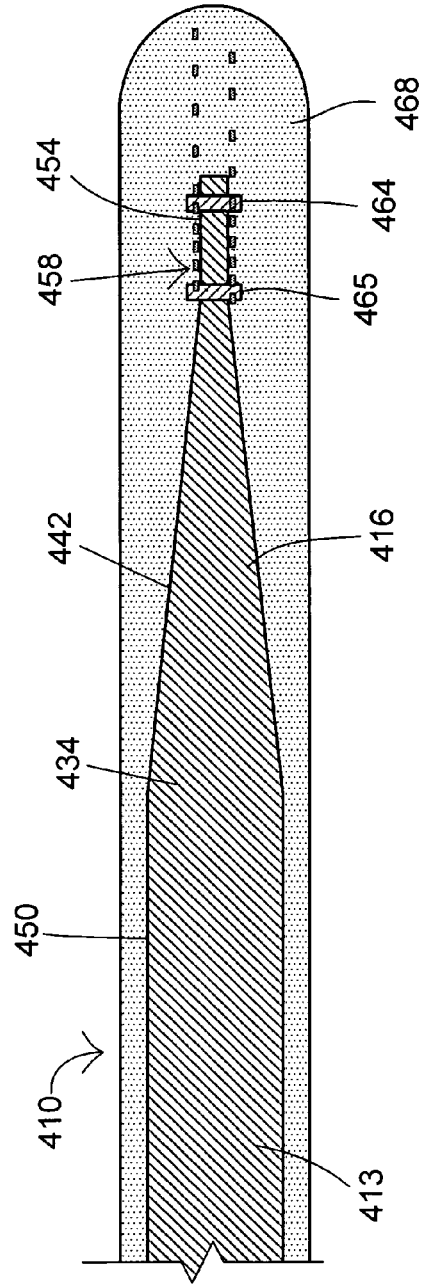

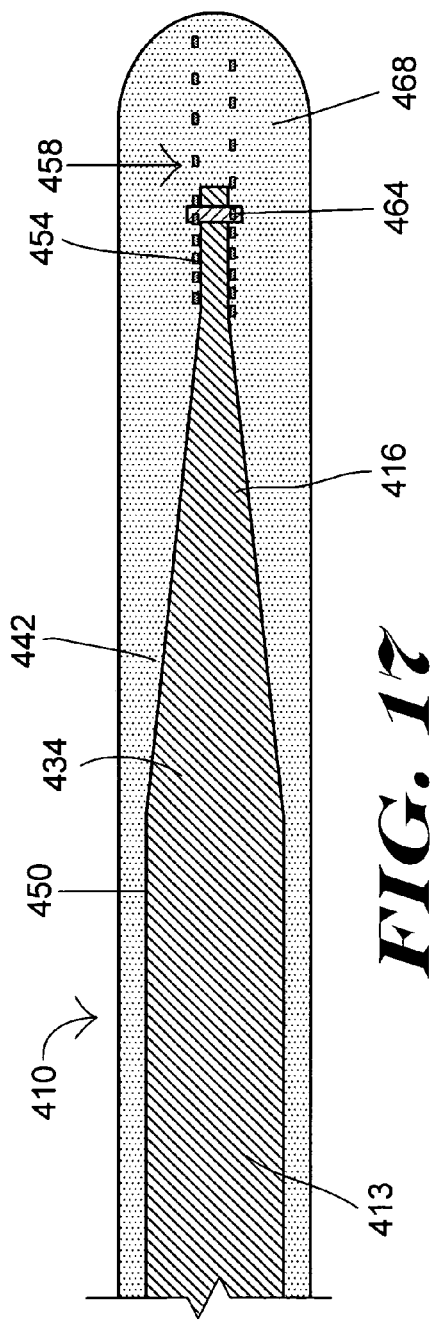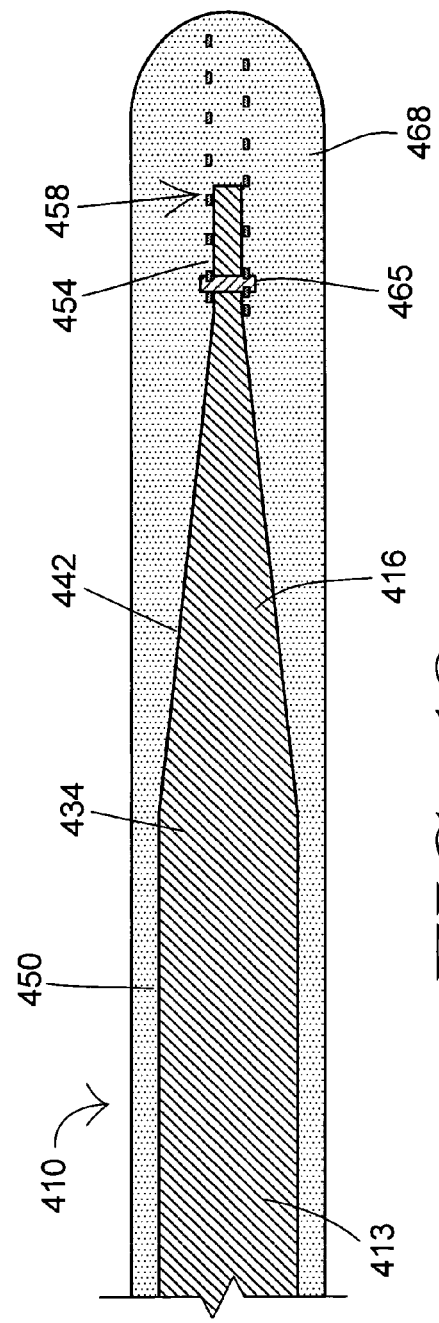

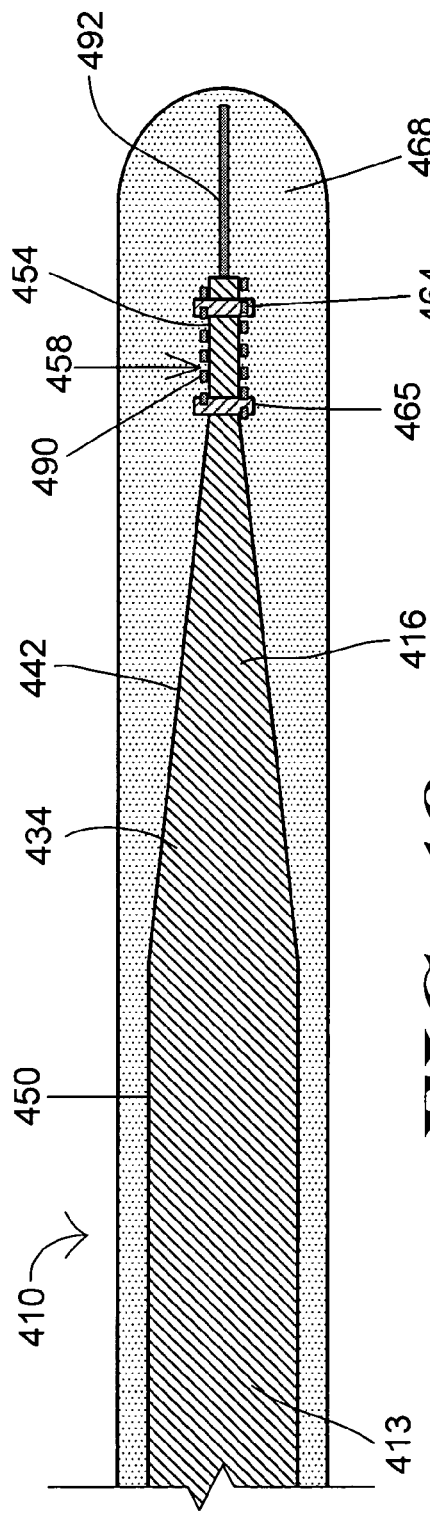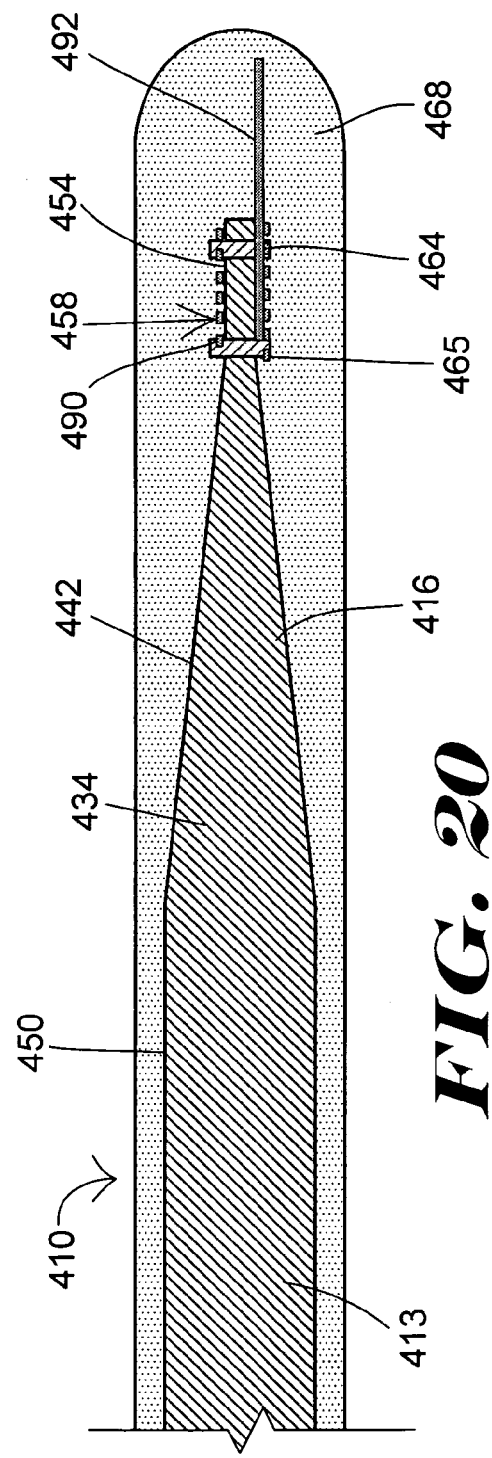

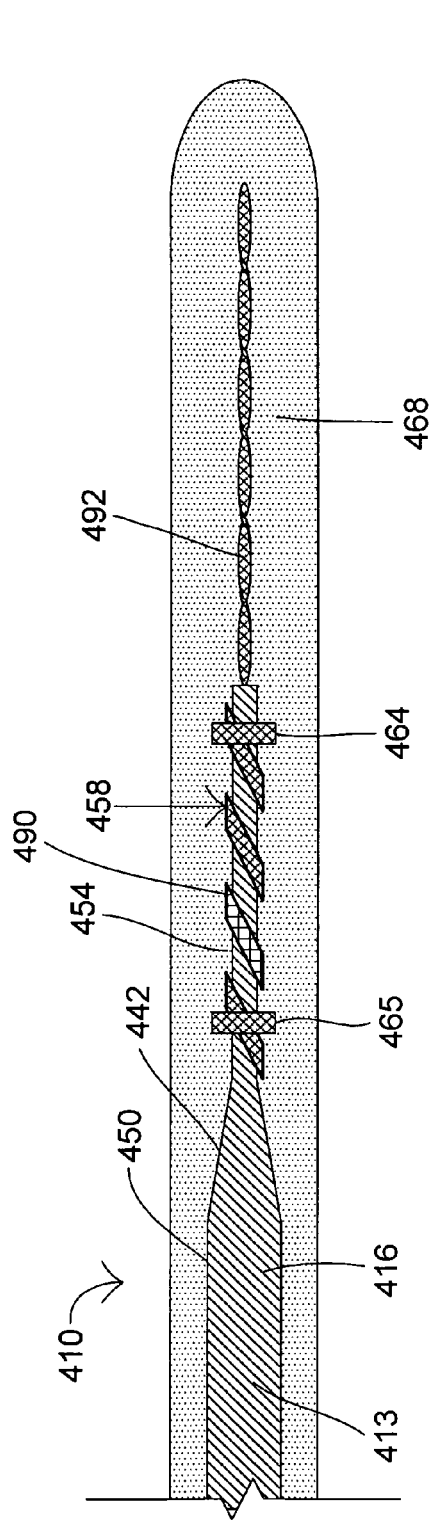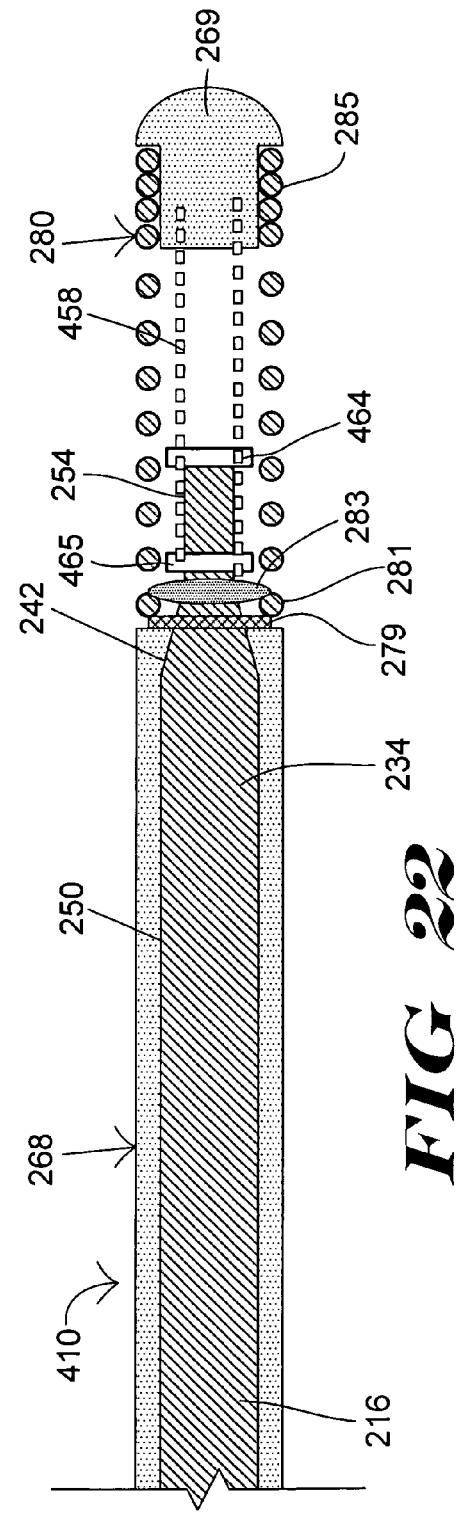

COMPOSITE GUIDEWIRE

RELATED APPLICATIONS

This is a continuation-in-part application of application Ser. No. 09/972,276 filed Oct. 5, 2001 now U.S. Pat. No. 6,918,882, which is incorporated herein by reference.

FIELD OF THE INVENTION

The invention generally pertains to intravascular guidewires.

BACKGROUND OF THE INVENTION

A wide variety of guidewires have been developed for intravascular use. Intravascular guidewires are commonly used in conjunction with intravascular devices such as catheters to facilitate navigation through the vasculature of a patient. Because the vasculature of a patient may be very tortuous, it is desirable to combine a number of performance features in an guidewire. For example, it is sometimes desirable that the guidewire have a relatively high level of pushability and torqueability, particularly near its proximal end. It is also sometimes desirable that a guidewire be relatively flexible, particularly near its distal end. A number of different guidewire structures and assemblies are known, each having certain advantages and disadvantages. However, there is an ongoing need to provide alternative guidewire structures and assemblies.

SUMMARY OF THE INVENTION

The invention provides several alternative designs, materials and methods of manufacturing alternative guidewire structures and assemblies.

BRIEF DESCRIPTION OF THE DRAWINGS

FIG. 7 is a cross sectional fragmentary view of an alternative guidewire construction including a connection similar to that shown in FIG. 2 utilizing an overlapping tapered joint and a tubular connector for joining a proximal section and a distal section of the guidewire, and also showing a distal tip construction;

FIG. 8 is a cross sectional fragmentary view of another alternative guidewire construction similar to that in FIG. 7, but including an alternative tip construction;

FIG. 9 is a cross sectional fragmentary view of another alternative guidewire construction similar to that in FIG. 7, but including another alternative tip construction;

FIG. 10 is a cross sectional fragmentary view of another alternative guidewire construction similar to that in FIG. 7, but including another alternative tip construction;

FIG. 13 is a cross sectional fragmentary view of another embodiment of a guidewire including an alternative tip construction.

FIG. 14 is a cross sectional fragmentary view of another embodiment of a guidewire including another alternative tip construction.

FIG. 15 is a cross sectional fragmentary view of another embodiment of a guidewire including another alternative tip construction.

FIG. 16 is a cross sectional fragmentary view of another embodiment of a guidewire including another alternative tip construction.

FIG. 17 is a cross sectional fragmentary view of another embodiment of a guidewire including another alternative tip construction.

FIG. 18 is a cross sectional fragmentary view of another embodiment of a guidewire including another alternative tip construction.

FIG. 19 is a cross sectional fragmentary view of another embodiment of a guidewire including another alternative tip construction.

FIG. 20 is a cross sectional fragmentary view of another embodiment of a guidewire including another alternative tip construction.

FIG. 21 is a cross sectional fragmentary view of another embodiment of a guidewire including another alternative tip construction.

FIG. 22 is a cross sectional fragmentary view of another embodiment of a guidewire including another alternative tip construction.

DETAILED DESCRIPTION OF THE INVENTION

Figure 1:
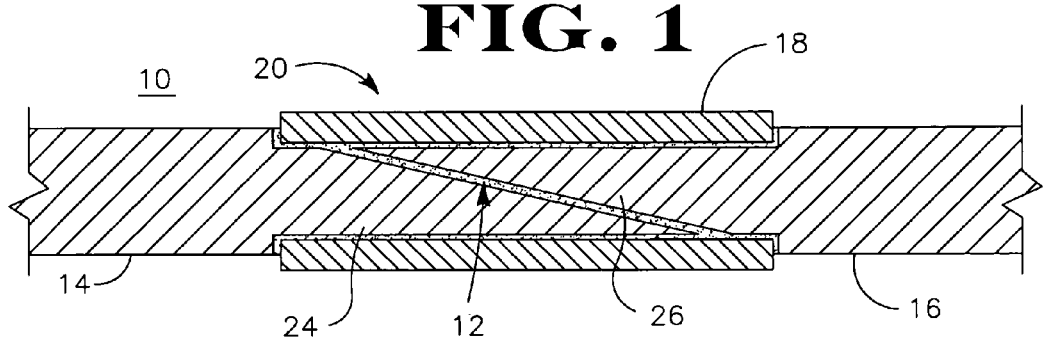
FIG. 1 is cross sectional fragmentary view of a guidewire (pre-grinding), including a connection utilizing an overlapping tapered joint and a tubular connector for joining a proximal section and a distal section of the guidewire.

The following description should be read with reference to the drawings wherein like reference numerals indicate like elements throughout the several views. The detailed description and drawings illustrate examples of various embodiments of the claimed invention, and are not intended to be limiting.

Figure 2:
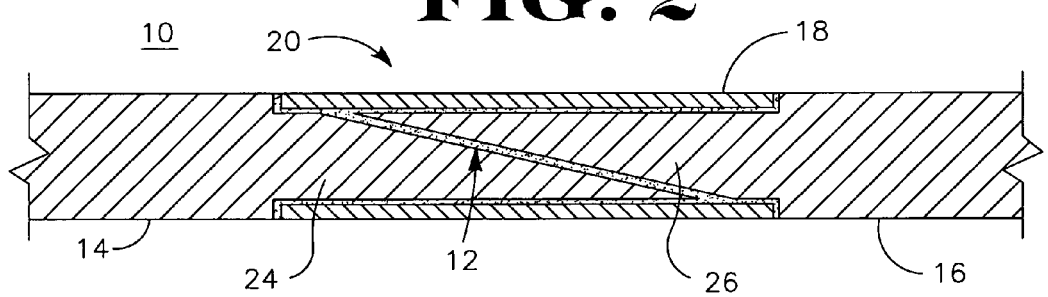
FIG. 2 is a cross sectional fragmentary view of the guidewire (post grinding) of FIG. 1.

Refer now to FIGS. 1–5 which illustrate cross sectional views of a portion of a guidewire 10 including a connection 20 joining a proximal guidewire section 14 and a distal guidewire section 16. FIG. 1 illustrates the guidewire 10 and the connection 20 before a final grinding step, and FIG. 2 illustrates the guidewire 10 and the connection 20 after the final grinding step, which provides a smooth outer profile.

The embodiment of FIGS. 1 and 2 utilizes an overlapping tapered joint 12 and a tubular connector 18.

Figure 3:
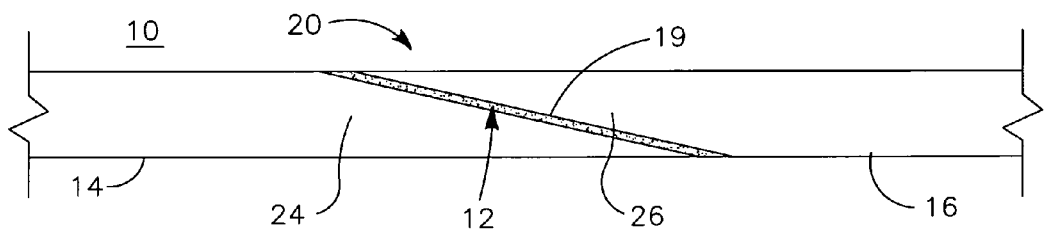
FIG. 3 is a cross sectional fragmentary view of an alternative guidewire (post grinding), including a connection utilizing an overlapping joint (without a tubular connector) for joining a proximal section and a distal section of the guidewire.
Figure 4:
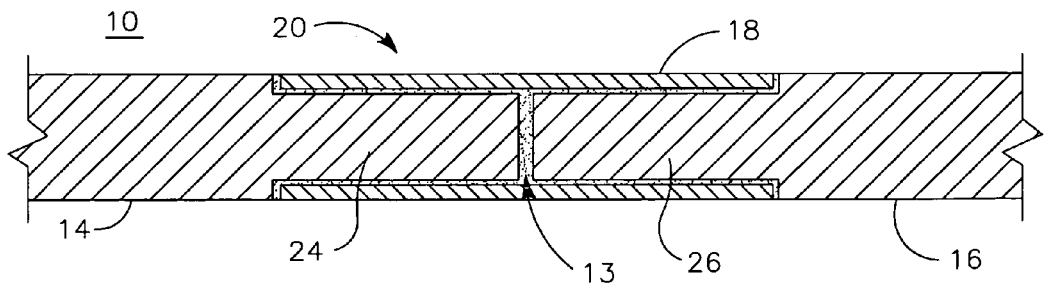
FIG. 4 is a cross sectional fragmentary view of an alternative guidewire (post grinding), including a connection utilizing a butt joint and a tubular connector for joining a proximal section and a distal section of the guide wire.
Figure 5:
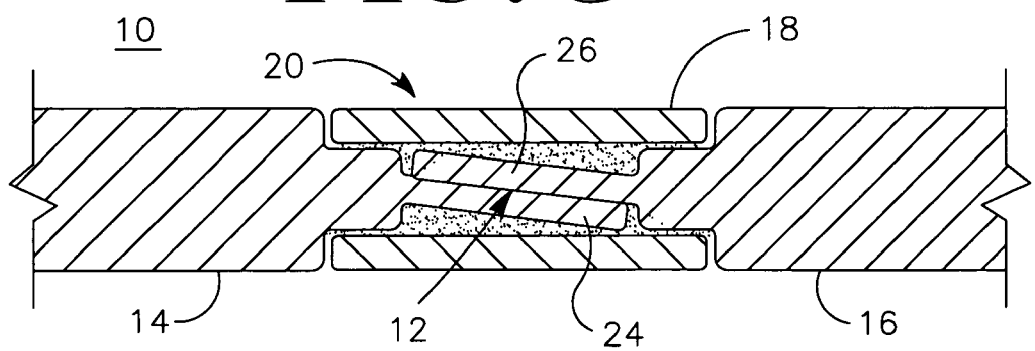
FIG. 5 is a cross sectional fragmentary view of an alternative guidewire (post grinding), including a connection utilizing an overlapping joint and a tubular connector for joining a proximal section and a distal section of the guide wire.

The embodiment of FIG. 3 is similar to the embodiment of FIGS. 1 and 2, except that the connection 20 between the proximal guidewire section 14 and the distal guidewire section 16 does not utilize a connector tube 18, but rather utilizes a connector material 19. The embodiment of FIG. 4 is similar to the embodiment of FIGS. 1 and 2, except that the connection 20 between the proximal guidewire section 14 and the distal guidewire section 16 does not utilize an overlapping joint 12, but rather uses a butt joint 13. The embodiment of FIG. 5 is also similar to the embodiment of FIGS. 1 and 2, except that the connection 20 between the proximal guidewire section 14 and the distal guidewire section 16 utilizes an overlapping joint 12 that is not tapered.

Those of skill in the art and others will recognize that the materials, structure, and dimensions of the proximal/distal guidewire sections 14/16 are dictated primary by the desired characteristics and function of the final guidewire, and that any of a broad range of materials, structures, and dimensions can be used.

For example, the proximal and distal guidewire sections 14/16 may have a solid cross-section as shown, or a hollow cross-section, and may be formed of any materials suitable for use, dependent upon the desired properties of the guidewire. Some examples of suitable materials include metals, metal alloys, and polymers. In some embodiments, it is desirable to use metals, or metal alloys that are suitable for metal joining techniques such as welding, soldering, brazing, crimping, friction fitting, adhesive bonding, etc. As used herein, the proximal section 14 and the distal section 16 may generically refer to any two adjacent guidewire sections along any portion of the guidewire. Furthermore, although discussed with specific reference to guidewires, the invention may be applicable to almost any intravascular device. For example, the invention may be applicable to hypotube shafts for intravascular catheters (e.g., rapid exchange balloon catheters, stent delivery catheters, etc.) or drive shafts for intravascular rotational devices (atherectomy catheters, IVUS catheters, etc.).

In some embodiments, the proximal guidewire section 14 may be formed of relatively stiff material such as straightened 304v stainless steel wire. Alternatively, proximal portion 14 may be comprised of a metal or metal alloy such as a nickel-titanium alloy, nickel-chromium alloy, nickel-chromium-iron alloy, cobalt alloy, or other suitable material. In general, the material used to construct proximal portion 14 may be selected to be relatively stiff for pushability and torqueability.

In some embodiments, the distal guidewire section 16 may be formed of a relatively flexible material such as a straightened super elastic or linear elastic alloy (e.g., nickel-titanium) wire, or a alternatively, a polymer material, such as a high performance polymer. Alternatively, distal portion 16 may be comprised of a metal or metal alloy such as stainless steel, nickel-chromium alloy, nickel-chromium-iron alloy, cobalt alloy, or other suitable material. In general, the material used to construct distal portion 16 may be selected to be relatively flexible for trackability.

In some particular embodiments, the distal section 16 is a linear elastic nickel-titanium alloy, for example, linear elastic nitinol. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

Within the family of commercially available nitinol alloys, is a category designated "linear elastic" which, although is similar in chemistry to conventional shape memory and superelastic varieties, exhibits distinct and useful mechanical properties. By skilled applications of cold work, directional stress, and heat treatment, the wire is fabricated in such a way that it does not display a "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range. For example, in some embodiments, there is no martensite/austenite phase changes detectable by DSC and DMTA analysis in the range of about −60° C. to about 120° C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy for the distal portion 16 allows the guidewire to exhibit superior "pushability" around tortuous anatomy.

In some embodiments, the linear elastic nickel-titanium alloy comprises in the range of about 50 to about 60 wt. % nickel, with the remainder being essentially titanium. In some particular embodiments, the composition comprises in the range of about 54 to about 57 wt. % nickel. One example of a suitable nickel-titanium alloy is FHP-NT alloy commercially available from Furukawa Techno Material Co. of Kanagawa, Japan.

In some particular embodiments, the proximal guidewire section 14 is formed from a stainless steel wire having a diameter in the range of 0.01 to 0.02 inches, and a length in the range of about 50 to about 110 inches, and the distal guidewire section 16 is formed from a linear elastic nitinol wire having a diameter that ranges from a diameter to match the diameter of the proximal guidewire section 14 to as small as about 0.002 inches, and a length in the range of 3 to 15 inches.

Figure 6A:
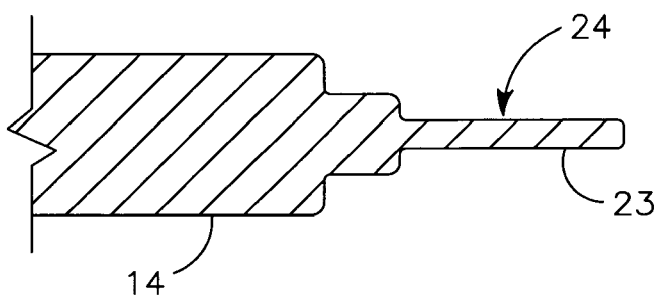
FIGS. 6A–6C are cross sectional fragmentary views of various end portions for use with the guidewire embodiment of FIG. 5.
Figure 6B:
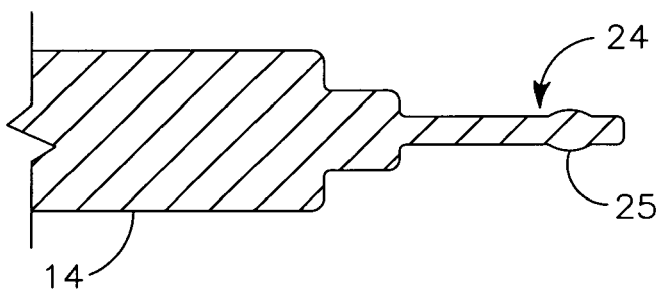
Figure 6C:
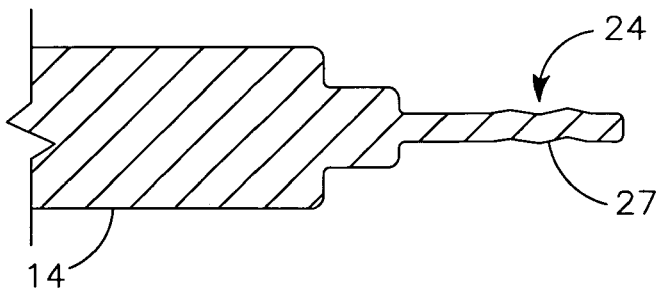

The distal end 24 of the proximal portion 14 and the proximal end 26 of distal portion 16 (i.e., the joined ends) may form an overlapping tapered joint 12 as shown in FIGS. 1–3. Alternatively, the joined ends 24/26 may form a butt joint 13 as shown in FIG. 4. As a further alternative, the joined ends 24/26 may form an overlapping joint 12 that is not tapered as shown in FIG. 5. The non-tapered end portions 24/26 may have a uniform profile (diameter) 23 as shown in FIG. 6A, a bulbous portion 25 for purposes of mechanical interlocking as shown in FIG. 6B, or a helical form 27 for purposes of mechanical interlocking as shown in FIG. 6C. In each of the embodiments illustrated in FIGS. 1–3 and 5, the end portions 24/26 overlap to form an overlapping joint 12. The overlapping joint 12 blends the stiffness of proximal portion 14 and distal portion 16 by combining the properties of each end section 24/26 making up the cross section of the overlapping joint 12. Thus, the joint 12 forms a flexibility transition region that has a relative flexibility that is between the flexibility of the proximal portion 14 and the flexibility of the distal portion 16.

In the tapered embodiments illustrated in FIGS. 1–3, the ends 24/26 may be tapered or otherwise formed to have a mating geometry that gradually decreases in cross sectional area toward the middle of the connection 20. The tapered overlapping portion 12 may define a uniform or a non-uniform transition of the sections 24/26, depending on the transition characteristics desired. For example, the end sections 24/26 may be linearly tapered as shown, tapered in a curvilinear fashion, or tapered in a step-wise fashion. If tapered linearly as shown, the angle of the taper may vary. Using the longitudinal center axis of the guidewire 10 as a reference, as measured from the extreme ends of the end sections 24/26, the angle of the taper is acute (i.e., less than 90 degrees), and may be in the range of 5 degrees to 45 degrees, for example. Varying the angle of the tapered ends 24/26 also varies the length of the overlapping joint 12 in accordance with geometric principles. The length of the overlapping joint 12 may be selected to obtain a more (longer length) or less (shorter length) gradual transition in stiffness.

As mentioned previously, the proximal guidewire section 14 and the distal guidewire section 16 may be formed of different materials (i.e., materials having different moduli of elasticity) resulting in a difference in flexibility. For example, the proximal guidewire section 14 may be formed of stainless steel wire and the distal guidewire section 16 may be formed of nickel-titanium alloy wire, both having the same dimensions, resulting in a 3:1 difference in elastic modulus. Such a difference in elastic modulus (i.e., flexibility) may result in a stress concentration point during flexure and/or torsion that may have a tendency to kink and fracture. By virtue of the gradual transition in stiffness provided by the overlapping portion 12, stress is distributed along the entire length of the connection 20 thereby decreasing the probability that guidewire 10 may kink at the junction.

A gradual transition in stiffness may also allow the connection 20 to be located further distally. According to this embodiment, the distal portion 16 may be manufactured to be shorter than proximal portion 14. Including a relatively long proximal section 14 may advantageously increase the torquability and pushability of the guidewire 10. Although only one connection 20 is shown, additional connections 20 may be used to connect other guidewire sections of varying stiffness.

The connector 18 may comprise a tubular structure such as a hypotube as shown or a coiled wire. The connector 18 may have an inside diameter sized appropriately to receive the ends 24/26 of the proximal portion 14 and the distal portion 16, and an outside diameter sufficient to accommodate a final grinding procedure. In some example embodiments, the connector 18 can have an inner diameter in the range of about 0.005 to about 0.02 inches, and an outer diameter in the range of about 0.01 to about 0.025 inches. In some particular embodiments, the connector 18 can have and inner diameter of about 0.010 inches and an outer diameter of about 0.014 inches. The final diameter of the guidewire 10 and the connector 18 may be in the range of 0.010 to 0.018 inches, for example. By way of example, not limitation, the connector 18 may have a length of about 1.0 to 3.0 inches for an overlapping portion 12 of about 0.25 to 2.5 inches. However, in some other embodiments, this type of construction can be applied to wires of larger diameter intended, for example, for peripheral intervention purposes. Such wires could range as large as 0.035 in diameter and therefore have an extended length connector and correspondingly longer overlapping sections.

The connector 18 may be comprised of a metal or metal alloy, and may include radiopaque materials. Suitable metals and metal alloys include stainless steels, nickel-titanium alloys (e.g., nitinol), nickel-chromium alloys, nickel-chromium-iron alloys, cobalt alloys, nickel, or other suitable materials. Alternatively, connector 18 may be comprised of a polymer or a metal-polymer composite, including a radiopaque filler.

Some types of alloys are particularly suitable for connector 18 for purposes of connecting a stainless steel proximal section 14 and a nickel titanium alloy distal section 16, or visa-versa. An example is a nickel-chromium-iron alloy designated UNS N06625 and is available under the trade name INCONEL 625, which advantageously welds to both stainless steels and nickel-titanium alloys. INCONEL 625 wire may be obtained from California Fine Wire Company of Grover Beach, Calif., and has the following typical composition:

| Material | Symbol | % by wgt |
| --- | --- | --- |
| Aluminum | Al | 0.140 |
| Carbon | C | 0.070 |
| Chromium | Cr | 21.900 |
| Cobalt | Co | 0.010 |
| Copper | Cu | 0.030 |
| Iron | Fe | 2.790 |
| Manganese | Mn | 0.030 |
| Molybdenum | Mo | 9.150 |
| Nickel | Ni | 62.000 |
| Niobium | Nb | 3.540 |
| Phosphorus | P | 0.005 |
| Silicon | Si | 0.230 |
| Sulfur | S | 0.009 |
| Titanium | Ti | 0.250 |
| Tantalum | Ta | 0.010 |

Another example of a suitable alloy which welds to both stainless steels and nickel-titanium alloys is designated UNS 10276 and is available under the trade name ALLOY C276 from Fort Wayne Metals Research Products Corporation of Fort Wayne, Ind., which has the following typical composition:

| Material | Symbol | % by wgt |
| --- | --- | --- |
| Carbon | C | 0.003 |
| Chromium | Cr | 15.810 |
| Cobalt | Co | 1.310 |
| Copper | Cu | 0.100 |
| Iron | Fe | 5.730 |
| Manganese | Mn | 0.520 |
| Molybdenum | Mo | 16.010 |
| Nickel | Ni | 57.000 |
| Phosphorus | P | 0.008 |
| Silicon | Si | 0.020 |
| Sulfur | S | 0.005 |
| Tungsten | W | 3.570 |
| Vanadium | V | 0.160 |

Another example of a suitable alloy which welds to both stainless steels and nickel-titanium alloys is of the Hastelloy family and an example of which is available under the trade name ALLOY B2 from Fort Wayne Metals Research Products Corporation of Fort Wayne, Ind., which has the following typical composition:

| Material | Symbol | % by wgt |
| --- | --- | --- |
| Carbon | C | 0.005 |
| Chromium | Cr | 0.450 |
| Cobalt | Co | 0.110 |
| Copper | Cu | 0.030 |
| Iron | Fe | 1.410 |
| Manganese | Mn | 0.150 |
| Molybdenum | Mo | 27.720 |
| Nickel | Ni | 70.000 |
| Phosphorus | P | 0.004 |
| Silicon | Si | 0.020 |
| Sulfur | S | 0.002 |
| Tungsten | W | 0.140 |

To manufacture the connection 20 of the guidewire 10, the ends 24/26 of the proximal and distal guidewire sections 14/16 may be ground to form the desired shape (e.g., uniform diameter 23, bulbous portion 25, helix 27, or taper) to accommodate the overlapping joint 12. If a butt joint 13 is to be used, such a shape need not be ground. A recess step may be ground into the proximal and distal guidewire sections 14/16 to accommodate the connector tube 18. If a connector tube 18 is not to be used, such a recess step need not be ground.

For the embodiments utilizing a connector tube 18, the connector tube 18 is positioned over one of the ends 24/26 of the proximal and distal guidewire sections 14/16. The distal end 24 of the proximal portion 14 and proximal end 26 of the distal portion 16 are then positioned adjacent one another in an overlapping 12 or an end-to-end 13 arrangement. The proximal and distal guidewire sections 14/16 and the connector tube 18 may be bonded, welded (e.g., resistance or laser welded), soldered, brazed, or otherwise connected by a suitable technique depending on the material selected for each component. Alternatively, the ends 24/26 and the connector tube 18 may be crimped together or may be sized to establish a friction fit therebetween. If a connector tube 18 is not used, the ends 24/26 may be bonded, welded (e.g., resistance or laser welded), soldered, brazed, or otherwise connected, using a connector material 19. Connector material 19 may be the same as or similar to the material of the connector 18. In all cases, because the connection 20 may reside within a catheter lumen during use, it is preferred that a permanent connection (as opposed to a releasable connection) be used.

It is to be appreciated that various welding processes may be utilized without deviating from the spirit and scope of the present invention. Examples of welding processes which may be suitable in some applications include LASER welding, resistance welding, TIG welding, microplasma welding, electron beam, and friction or inertia welding. LASER welding equipment which may be suitable in some applications is commercially available from Unitek Miyachi of Monrovia, Calif. and Rofin-Sinar Incorporated of Plymouth, Mich. Resistance welding equipment which may be suitable in some applications is commercially available from Palomar Products Incorporated of Carlsbad, Calif. and Polaris Electronics of Olathe, Kans. TIG welding equipment which may be suitable in some applications is commercially available from Weldlogic Incorporated of Newbury Park, Calif. Microplasma welding equipment which may be suitable in some applications is commercially available from Process Welding Systems Incorporated of Smyrna, Tenn.

Once connected, the connector tube 18 and the proximal and distal guidewire sections 14/16 are centerless ground to provide a smooth and uniform profile across the connection 20, and to straighten out small misalignments between the proximal and distal guidewire sections 14/16. Other portions of the guidewire 10 may be ground as well to provide the desired tapers and changes in diameter. For example, one or both of the proximal and distal guidewire sections 14/16 can be continuously tapered, can have a tapered section or a number or series of tapered sections of differing diameters, or can have a constant diameter. In some embodiments, the sections 14/16 are tapered or otherwise formed to have a geometry that decreases in cross sectional area toward the distal end thereof. If tapered, the sections 14/16 can include a uniform or a non-uniform transition of the sections, depending on the transition characteristics desired. For example, one or both of the sections 14/16 may be linearly tapered, tapered in a curvilinear fashion, or tapered in a step-wise fashion. The angle of any such tapers can vary, depending upon the desired flexibility characteristics. The length of the taper may be selected to obtain a more (longer length) or less (shorter length) gradual transition in stiffness. Once finally ground, in some embodiments, a flexible coil tip and/or a polymer jacket tip (optionally covering connection 20) or combination thereof, and other such structure, such as radiopaque markers, safety and/or shaping ribbons (coiled or uncoiled), and the like, may be placed on the guidewire 10. Additionally, in some embodiments, a coating, for example a lubricious (e.g., hydrophylic) or other type of coating may be applied to all or portions of the guidewire. Different coatings can be applied to different sections of the guidewire. Some examples of such coatings and materials and methods used to create such coatings can be found in U.S. Pat. Nos. 6,139,510 and 5,772,609, which are incorporated herein by reference.

The centerless grinding technique may utilize an indexing system employing sensors (e.g., optical/reflective, magnetic) to avoid excessive grinding of the connection 20. In some embodiments, the presence of dissimilar materials in the construction can influence the grinding technique and tooling used to accomplish uniform material removal, create smooth transitions, and successfully bridge across adjacent components. In addition, the centerless grinding technique may utilize a CBN or diamond abrasive grinding wheel that is well shaped and dressed to avoid grabbing the connector 20 during the grinding process.

Refer now to FIG. 7, which shows a cross sectional view of a portion of a guidewire 110 including a connection 120 similar to the connection 20 shown in the embodiment of FIG. 1. The connection 120 utilizes an overlapping tapered joint 112 and a tubular connector 118 joining a proximal guidewire section 114 and a distal guidewire section 116. The proximal/distal guidewire sections 114/116, the connection 120, the tapered joint 112, and the tubular connector 118 shown in the embodiment of FIG. 7 can include the same general construction, structure, materials, and methods of construction as discussed above with regard to like components in the embodiments of FIGS. 1–6C.

The embodiment of FIG. 7 also shows one example of a distal tip portion 130 of the guidewire 110 disposed at the distal end portion 134 of the distal guidewire section 116. The distal end portion 134 includes two tapered regions 142 and 146, and two constant diameter regions 150 and 154 such that the end portion 134 has a geometry that decreases in cross sectional area toward the distal end thereof. In some embodiments, these tapers 142/146 and constant diameter regions 150/154 are adapted and configured to obtain a transition in stiffness, and provide a desired flexibility characteristic.

A wire or ribbon 158 is attached adjacent the distal end 160 of the distal end portion 134, and extends distally of the distal end portion 134. In some embodiments, the wire or ribbon 158 can be a fabricated or formed wire structure, for example a coiled wires, as will be seen in embodiments discussed in more detail below. In the embodiment shown, the ribbon 158 is a generally straight wire that overlaps with and is attached to the constant diameter region 154 at attachment point 164. In some embodiments, the ribbon 158 overlaps with the constant diameter section 154 by a length in the range of about 0.05 to 1.0 inch, but in other embodiments, the length of the overlap can be greater or less.

The ribbon 158 can be made of any suitable material and sized appropriately to give the desired characteristics, such as strength and flexibility characteristics. Some examples of suitable materials include metals, metal alloys, polymers, and the like. In some embodiments, the ribbon 158 may be formed of a metal or metal alloy such as stainless steel, nickel-chromium alloy, nickel-chromium-iron alloy, cobalt alloy, a nickel-titanium alloy, such as a straightened super elastic or linear elastic alloy (e.g., nickel-titanium) wire. The ribbon 158 can be attached using any suitable attachment technique. Some examples of attachment techniques include soldering, brazing, welding, adhesive bonding, crimping, or the like. In some embodiments, the ribbon or wire 158 can function as a shaping structure or a safety structure.

An outer sleeve 168 is disposed about the distal end portion 134 of the distal guidewire section 116. In the embodiment shown, the sleeve 168 extends from the proximal tapered region 142 to beyond the distal most portion of the ribbon 158, and forms a rounded tip portion 169. In other embodiments, the sleeve 158 can extend further in a proximal direction, and in some cases can extend over the connection 120, or over the proximal guidewire section 114. In yet other embodiments, the sleeve 168 can begin at a point distal of the tapered region 142.

Suitable material for use as the outer sleeve 168 include any material that would give the desired strength, flexibility or other desired characteristics. Some suitable materials include polymers, and like material. Examples of suitable polymer material include any of a broad variety of polymers generally known for use as guidewire polymer sleeves. The use of a polymer for outer sleeve 168 can serve several functions. The use of a polymer sleeve can improve the flexibility properties of the distal portion 134. Choice of polymers for the sleeve 168 will vary the flexibility. For example, polymers with a low durometer or hardness will make a very flexible or floppy tip. Conversely, polymers with a high durometer will make a tip which is stiffer. The use of polymers for the sleeve can also provide a more atraumatic tip for the guide wire. An atraumatic tip is better suited for passing through fragile body passages. Finally, a polymer can act as a binder for radiopaque materials, as discussed in more detail below.

In some embodiments, the polymer material used is a thermoplastic polymer material. Some examples of some suitable materials include polyurethane, elastomeric polyamides, block polyamide/ethers (such as Pebax), silicones, and co-polymers. The sleeve may be a single polymer, multiple layers, or a blend of polymers. By employing careful selection of materials and processing techniques, thermoplastic, solvent soluble, and thermosetting variants of these materials can be employed to achieve the desired results.

The sleeve 168 can be disposed around and attached to the guidewire 110 using any suitable technique for the particular material used. In some embodiments, the sleeve 168 is attached by heating a sleeve of polymer material to a temperature until it is reformed around the distal guidewire section 116 and the ribbon 158. In some other embodiments, the sleeve 168 can be attached using heat shrinking techniques. The sleeve 168 may be finished, for example, by a centerless grinding or other method, to provide the desired diameter and to provide a smooth outer surface.

In some embodiments, the sleeve 168, or portions thereof, can include, or be doped with, radiopaque material to make the sleeve 168, or portions thereof, more visible when using certain imaging techniques, for example, fluoroscopy techniques. Any suitable radiopaque material known in the art can be used. Some examples include precious metals, tungsten, barium subcarbonate powder, and the like, and mixtures thereof. In some embodiments, the sleeve 168 can include different sections having different amounts of loading with radiopaque material. For example, in FIG. 7, the sleeve 168 includes a distal section 170, and a proximal section 172, wherein the distal section 170 has a higher level of loading with radiopaque material than the proximal section 172. In some embodiments, it is also contemplated that a separate radiopaque member or a series of radiopaque members, such as radiopaque coils, bands, tubes, or other such structures could be attached to the guidewire 110, or incorporated into the core wire by plating, drawing, forging, or ion implantation techniques.

Additionally, in some embodiments, a coating, for example a lubricious (e.g., hydrophylic) or other type of coating may be applied over portions or all of the sleeve, or other portions of the guidewire 110. Hydrophobic coatings such as fluoropolymers provide a dry lubricity which improves guide wire handling and device exchanges. Lubricious coatings improve steerability and improve lesion crossing capability. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the more distal portion of the guidewire is coated with a hydrophilic polymer as discussed above, and the more proximal portions is coated with a fluoropolymer, such as polytetrafluroethylene (PTFE).

It will be understood by those of skill in the art and others that a broad variety of materials, dimensions, and structures can be used to construct suitable embodiments, depending upon the desired characteristics. The following examples of some dimensions for the distal construction are included by way of example only, and are not intended to be limiting. In some specific embodiments, the guidewire has the general structure set fourth in FIG. 7, and the distal guidewire section 116 has a length in the range of about 10 to 20 inches. The main portion of the distal guidewire section 116 has an outer diameter in the range of 0.013 to about 0.0145 inches, and the two constant diameter regions 150 and 154 have an outer diameter in the range of about 0.0094 to about 0.0097 and in the range of 0.001 to about 0.0014 respectively. The two constant diameter regions 150 and 154 have a length in the range of about 4 to about 15 inches and in the range of about 0.5 to about 4 inches respectively. The two tapered regions 142 and 146 have lengths in the range of about 0.5 to about 2 inches and in the range of about 0.5 to about 2 inches, respectively. The polymer sleeve 168 has an outer diameter sized to match the outer diameter of the main portion of the distal guidewire section 116, for example in the range of about 0.013 to about 0.0145 inches. The polymer sleeve distal section 170, is loaded with a radiapaque material, and has a length in the range of about 1 to about 3 inches. The ribbon 158 has a length in the range of about 0.8 to about 2 inches, and in some embodiments can extend about 0.2 to about 1 inch distally of the core.

FIG. 8 shows a guidewire 110 very similar to that shown in FIG. 7, wherein like reference numerals indicate similar structure as discussed above. The proximal/distal guidewire sections 114/116, the connection 120, the tapered joint 112, and the tubular connector 118 shown in the embodiment of FIG. 8 can also include the same general construction, structure, materials, and methods of construction as discussed above with regard to like components in the embodiments of FIGS. 1–7.

The distal tip portion 130 of the guidewire 110 of FIG. 8 is also very similar to that shown in FIG. 7, wherein like reference numerals indicate similar structure. In the embodiment shown in FIG. 8, however, the ribbon 158 extends further in a proximal direction to overlap with the tapered region 146, and is attached at two attachment points 164 and 165.

Refer now to FIG. 9, which shows a cross sectional view of a portion of another embodiment of a guidewire 210 including a connection 220 similar to that shown in the embodiments of FIGS. 7 and 8. The proximal/distal guidewire sections 214/216, the connection 220, the tapered joint 212, and the tubular connector 218 shown in the embodiment of FIG. 9 can include the same general construction, structure, materials, and methods of construction as discussed above with regard to like components in the embodiments of FIGS. 1–8.

The embodiment of FIG. 9 shows another example of a distal tip portion 230 of the guidewire 210 disposed at the distal end portion 234 of the distal guidewire section 216. Like the embodiment of FIG. 7, the distal end portion 234 includes two tapered regions 242. and 246, and two constant diameter regions 250 and 254 such that the end portion 234 has a geometry that decreases in cross sectional area toward the distal end thereof. Additionally, the distal tip portion 230 also includes a wire or ribbon 258 that is attached adjacent the distal end 260 of the distal end portion 234 at attachment point 264 in a similar manner as taught above in the embodiment of FIG. 7.

In FIG. 9, however, the distal tip portion 230 includes a combination of a sleeve 268 and a coil 280 disposed about the distal end portion 234 of the distal guidewire section 216. The sleeve 268 extends from the proximal tapered region 242 to a point proximal of the distal end of the guidewire section 216. In the embodiment shown, the sleeve 268 extends from the tapered region 242 to about midway through the tapered portion 246. In other embodiments, the sleeve 268 can extend further in a proximal direction, and in some cases can extend over the connection 220, or over the proximal guidewire section 214. In yet other embodiments, the sleeve 268 can begin at a point distal of the tapered region 242.

The sleeve 268 can be made of and include the same materials, structure, radiopaque loading, and coatings, and be made in accordance with the same methods as discussed above with regard to the embodiments shown in FIGS. 1–8. In the embodiment shown, an adhesive material or potting compound 279 is disposed at the distal end 265 of the sleeve 268 about the distal guidewire section 216. However, in other embodiments, the adhesive material or potting compound 279 is not used.

The coil 280 extends from the adhesive material 279 adjacent the distal end 265 of the sleeve 268 to beyond the distal most portion of the ribbon 258. The coil 280 is attached to the distal guidewire section 216 at its proximal end 281 at attachment point 283 using any suitable attachment technique, for example soldering, brazing, welding, adhesive bonding, crimping, or the like. The distal end 285 of the coil 280 is attached to the ribbon 258 via a rounded tip portion 269. The rounded tip portion 269 can be made of any suitable material, for example a solder tip, a polymer tip, and the like.

The coil 280 may be made of a variety of materials including metals, metal alloys, polymers, and the like. Some examples of material for use in the coil include stainless steel, nickel-chromium alloy, nickel-chromium-iron alloy, cobalt alloy, or other suitable materials. Some additional examples of suitable material include straightened super elastic or linear elastic alloy (e.g., nickel-titanium) wire, or alternatively, a polymer material, such as a high performance polymer. In some embodiments, the coil 280 can be made of a radiopaque materials such as gold, platinum, tungsten, or the like, or alloys thereof. The coil 280 may be formed of round or flat ribbon ranging in dimensions to achieve the desired flexibility. In some embodiments, the coil 280 may be a round ribbon in the range of about 0.001–0.015 inches in diameter, and can have a length in the range of about 2 to about 4 inches.

The coil 280 is wrapped in a helical fashion by conventional winding techniques. The pitch of adjacent turns of coil 280 may be tightly wrapped so that each turn touches the succeeding turn or the pitch may be set such that coil 280 is wrapped in an open fashion. In the embodiment shown, the coil 280 is wrapped such that the coil 280 has an open wrap at its proximal end 281, and includes a tightly wrapped portion adjacent the tip 269.

Additionally, in some embodiments, a coating, for example a lubricious (e.g., hydrophylic) or other type of coating similar to that discussed above may be applied over portions or all of the sleeve 268 and coil 280, or other portions of the guidewire 210.

It will be understood by those of skill in the art and others that a broad variety of materials, dimensions, and structures can be used to construct suitable embodiments, depending upon the desired characteristics. The examples of some dimensions for the distal construction included with reference to FIG. 7 are also suitable for the embodiment shown in FIG. 9.

FIG. 10 shows a guidewire 210 very similar to that shown in FIG. 9, wherein like reference numerals indicate similar structure. The proximal/distal guidewire sections 214/216, the connection 220, the tapered joint 212, and the tubular connector 218 shown in the embodiment of FIG. 10 can also include the same general construction, structure, materials, and methods of construction as discussed above with regard to like components in the embodiments of FIGS. 1–9.

The distal tip portion 230 of the guidewire 210 of FIG. 10 is also very similar to that shown in FIG. 9, wherein like reference numerals indicate similar structure. In the embodiment shown in FIG. 10, however, the ribbon 258 extends further in a proximal direction to overlap with the tapered region 246, and is attached at two attachment points 264 and 283.

Figure 11:
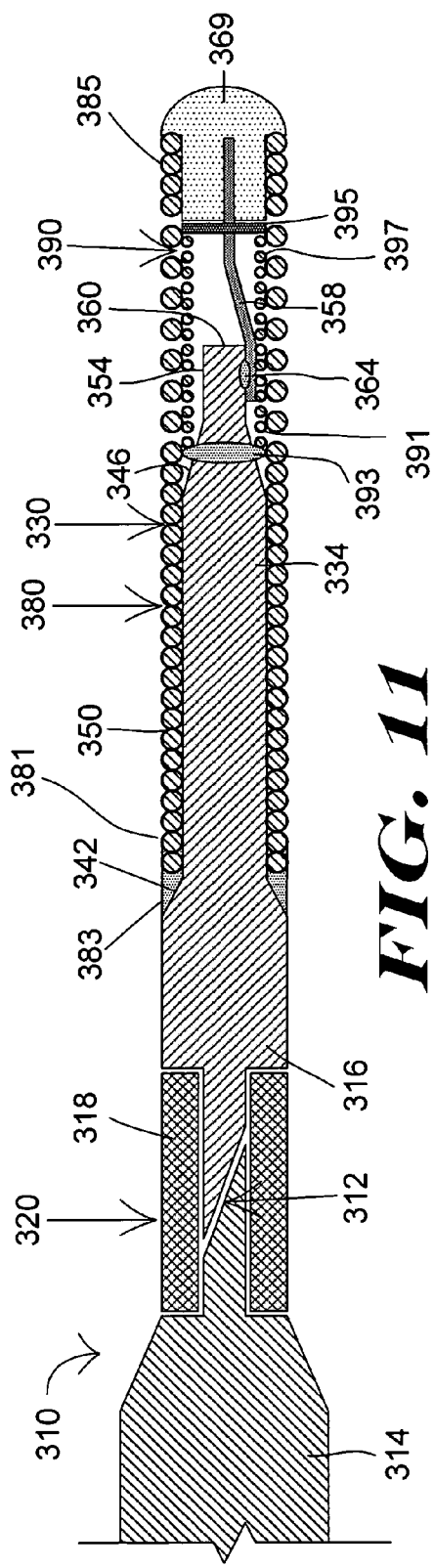
FIG. 11 is a cross sectional fragmentary view of another alternative guidewire construction similar to that in FIG. 7, but including another alternative tip construction.

Refer now to FIG. 11, which shows a cross sectional view of a portion of another embodiment of a guidewire 310 including a connection 320 similar to that shown in the embodiments of FIGS. 7–10. The proximal/distal guidewire sections 314/316, the connection 320, the tapered joint 312, and the tubular connector 318 shown in the embodiment of FIG. 11 can include the same general construction, structure, materials, and methods of construction as discussed above with regard to like components in the embodiments of FIGS. 1–10.

The embodiment of FIG. 11 shows another example of a distal tip portion 330 of the guidewire 310 disposed at the distal end portion 334 of the distal guidewire section 316. Like the embodiment of FIGS. 7–10, the distal end portion 334 includes two tapered regions 342 and 346, and two constant diameter regions 350 and 354 such that the end portion 334 has a geometry that decreases in cross sectional area toward the distal end thereof. Additionally, the distal tip portion 330 also includes a wire or ribbon 358 that is attached adjacent the distal end 360 of the distal end portion 334 at attachment point 364 in a similar manner as taught above in the embodiments of FIGS. 7 and 9.

In FIG. 11, however, the distal tip portion 330 includes a dual coil tip construction having an outer coil 380 and an inner coil 390 disposed about the distal end portion 334 of the distal guidewire section 316.

In the embodiment shown, the outer coil 380 extends about the distal guidewire section 316 from the tapered region 342 to beyond the distal most portion of the ribbon 358. The outer coil 380 is attached to the distal guidewire section 316 at its proximal end 381 at attachment point 383 using any suitable attachment technique, for example soldering, brazing, welding, adhesive bonding, crimping, or the like. The distal end 383 of the coil 380 is attached to the ribbon 358 via a rounded tip portion 369. The rounded tip portion 369 can be made of any suitable material, for example a solder tip, a polymer tip, and the like. The outer coil 380 can be made of the same materials, and have the same general construction and pitch spacing as the coil 280 discussed above in the embodiments of FIGS. 9 and 10. In some embodiments, the outer coil 280 can extend distally beyond attachment point 393 for a length in the range of about 2 to about 4 centimeters.

In the embodiment shown, the inner coil 390 is disposed about the distal guidewire section 316 from the tapered region 346 to a spacer element 395 adjacent the tip portion 369. In other embodiments, however, the spacer element is not required. The coil 390 is attached to the distal guidewire section 316 at its proximal end 391 at attachment point 393 using any suitable attachment technique, for example soldering, brazing, welding, adhesive bonding, crimping, or the like. The distal end 397 of the coil 390 is attached to the spacer element 395. The spacer element 395 is disposed about the ribbon 358, and can be made of any suitable material, for example metal, metal alloy, or a polymer, or the like. In some embodiments, the spacer is made of a polymer such as polytetrafluroethylene (PTFE).

The inner coil 390 can be made of the same materials, and have the same general construction and pitch spacing as discussed above with regard to the coil 280 in the embodiments of FIGS. 9 and 10. In some embodiments, the inner coil 390 is made of a radiopaque wire having a diameter less than that of the wire used to make the outer coil 380.

It will be understood by those of skill in the art and others that a broad variety of materials, dimensions, and structures can be used to construct suitable embodiments, depending upon the desired characteristics. The examples of some dimensions for the distal construction included with reference to FIG. 7 are also suitable for the embodiment shown in FIGS. 9 and 11.

Figure 12:
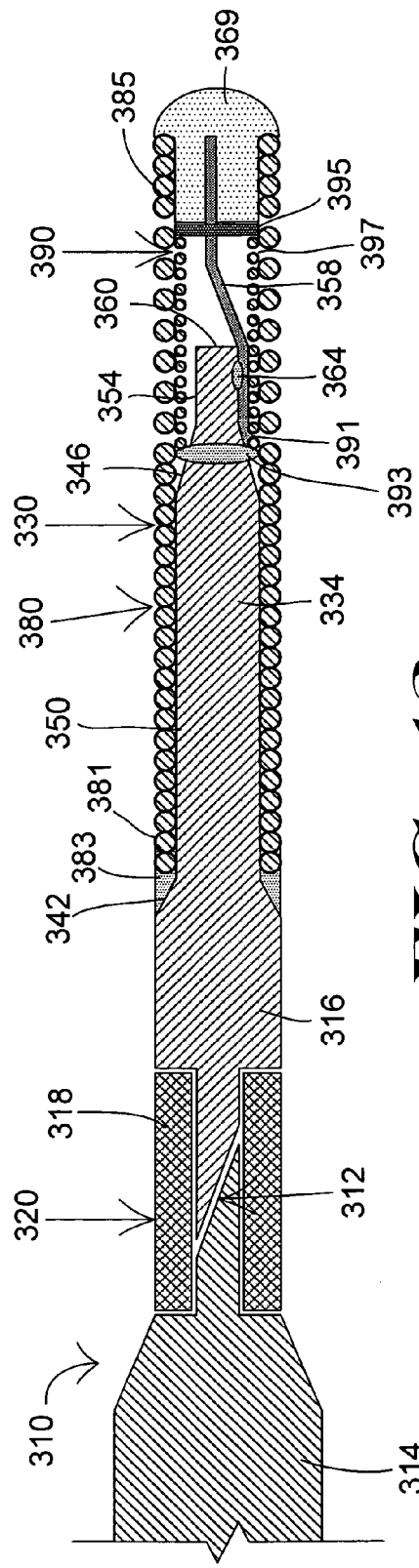
FIG. 12 is a cross sectional fragmentary view of another alternative guidewire construction similar to that in FIG. 7, but including another alternative tip construction.

FIG. 12 shows a guidewire 310 very similar to that shown in FIG. 11, wherein like reference numerals indicate similar structure. The proximal/distal guidewire sections 314/316, the connection 320, the tapered joint 312, and the tubular connector 318 shown in the embodiment of FIG. 12 can also include the same general construction, structure, materials, and methods of construction as discussed above with regard to like components in the embodiments of FIGS. 1–11.

The distal tip portion 330 of the guidewire 310 of FIG. 12 is also very similar to that shown in FIG. 11, wherein like reference numerals indicate similar structure. In the embodiment shown in FIG. 12, however, the ribbon 358 extends further in a proximal direction to overlap with the tapered region 346, and is attached at two attachment points 364 and 393.

Refer now to FIGS. 13–21, which show a series of alternative tip designs for use in guidewires which include a coiled or helically shaped portion of wire or ribbon for use as a safety and/or shaping structure. Such tip designs using a coiled or helically shaped safety or shaping structure can be used in a broad variety of guidewire structures. For example, these tip designs can be used in combination with other structure disclosed herein, such as the connector structures discussed above, or can be used in other guidewire constructions, for example guidewires that do not include such connector structures.

Refer now to FIG. 13, which shows one embodiment of a guidewire 410 having a coiled safety and/or shaping structure 458. The guidewire 410 includes a core member 413 having a distal portion 416. The core member 413, and the distal portion 416 thereof, can include structure as disclosed above for portions of a guidewire, or can include other structure generally known in the art for use in guidewires. Additionally, the core member 413, and the distal portion 416 thereof, can be made using any of the suitable materials discussed above for use in making guidewire members or sections, or can include other materials generally known in the art for use in guidewires. In the embodiment shown, the distal portion 416 of the core member 413 is a solid wire that has a tip portion 434 including three constant diameter portions 450, 452 and 454, and two tapered portions 442 and 446.

The coiled safety and/or shaping structure 458, for example a coiled ribbon, a coiled wire, or other such coiled structure, is disposed about a portion of the core wire 413. In the embodiment shown, the coiled structure 458 is a coiled ribbon that overlaps with or surrounds a portion of the distal most tapered portion 446 and the distal most constant diameter portion 454, and then extends distally from the distal end 460 of the core wire 413.

The coil 458 can be made of any suitable material and sized appropriately to give the desired characteristics, such as strength and flexibility characteristics. In some embodiments, the attachment of the coil 458 to the core wire 413 can also influence the characteristics of the portion of the core wire 413 overlapped by the coil 458.

Some examples of material for use in the coil 458 include stainless steel, nickel-chromium alloy, nickel-chromium-iron alloy, cobalt alloy, nickel-titanium alloy, or other suitable materials. Some additional examples of suitable material include straightened super elastic or linear elastic alloy (e.g., nickel-titanium), or alternatively, a polymer material, such as a high performance polymer. In some embodiments, the coil 458 can be made of a radiopaque materials such as gold, platinum, tungsten, or the like, or alloys thereof. The coil 458 may be formed of round or flat ribbon ranging in dimensions to achieve the desired flexibility. In some embodiments, the coil 458 may be a round wire in the range of about 0.001–0.015 inches in diameter. In some other embodiments, the coil can be made of a flat or rectangular shaped ribbon having a width in the range of about 0.002 to 0.02 inches and a thickness in the range of about 0.0005 to about 0.02 inches.

The coil 458 can be attached to the core wire 413 using any suitable attachment technique. Some examples of attachment techniques include soldering, brazing, welding, adhesive bonding, crimping, or the like. In the embodiment shown, the coil 458 is attached at two attachment points 464 and 465.

The coil 458 is wrapped in a helical fashion by conventional winding techniques. The pitch of adjacent turns of coil 458 may be tightly wrapped so that each turn touches the succeeding turn or the pitch may be set such that coil 458 is wrapped in an open fashion. In some embodiments, the coil can have a pitch of up to about 0.4 inches, in some embodiments a pitch of up to about 0.08 inches, and in some embodiments, a pitch in the range of about 0.01 to about 0.08 inches. The pitch can be constant throughout the length of the coil 458, or can vary, depending upon the desired characteristics, for example flexibility. In some embodiments, the pitch of the coil 458 portion that overlaps with the core wire 413 is smaller, while the pitch of the coil portion that does not overlap with the core wire 413 is larger. For example, in some embodiments, the pitch of the coil portion that overlaps with the core wire 413 is in the range of 0.01 to 0.08 inches, for example 0.04 inches, while the pitch of the coil portion that does not overlap with the core wire 413 is up to about 0.08 inches. These changes in coil pitch can be achieved during the initial winding of the wire, or can be achieved by manipulating the coil after winding or after attachment to the guidewire. For example, in some embodiments, after attachment of the coil 458 to the guidewire, a larger pitch can be achieved on the distal portion of the coil by simply pulling the coil.

The diameter of the coil 458 is preferably sized to fit around and mate with the distal portion of the core wire 413, and to give the desired characteristics. The diameter of the coil 458 can be constant or tapered. In some embodiments, the coil 458 is tapered to mate with tapered sections of the core wire 413. The diameter of the coil 458 can also include a taper beyond the distal end of the core wire 413, as desired.

An outer sleeve 468 is disposed about the distal portion 416 of the guidewire 410. In the embodiment shown, the sleeve 468 extends beyond the distal most portion of the coiled ribbon 458, and forms a rounded tip portion 469. The sleeve 468 can include structures, and be made with the materials and methods discussed above with regard to sleeve structures.

It will be understood by those of skill in the art and others that a broad variety of materials, dimensions, and structures can be used to construct suitable embodiments, depending upon the desired characteristics. The following examples are included by way of example only, and are not intended to be limiting. In some specific embodiments, the guidewire has the general structure set fourth in FIG. 13, wherein the core wire 413 is a distal portion of a core wire made of linear elastic nickel-titanium alloy, wherein the constant diameter portions 450, 452 and 454 are about 0.0097 inches, 0.006 inches, and 0.003 inches in diameter, respectively. Additionally, the constant diameter portions 452 and 454 are about 1 inch and 0.5 inches in length, respectively. The tapered portions 442 and 446 are about 1 inch and 1.5 inches, respectively. The coil 458 is about 1.5 inches long, is made of flattened stainless steel wire having width and thickness dimensions of about 0.005 inches by about 0.001 inches. The coil 458 has a diameter that is tapered from about 0.0097 inches on its proximal end to about 0.003 inches on its distal end, and is attached to the core wire 413 at attachment points 464 and 465 using solder. The coil 458 overlaps the core wire 413 for about 1.1 inches, and extends distally of the core wire 413 for about 0.4 inches. The pitch of the coil portion that overlaps the core wire is about 0.04 inches and the pitch of the coil portion that extends distally of the core wire is about 0.08 inches. In some such embodiments, the portion of the guidewire where the coil 458 overlaps the core wire 413 for about 1.1 inches is plated, for example, with tin plating. The sleeve 468 is a polyurethane sleeve attached about the core wire 413 and coil 458. A hydrophilic coating is then coated onto the sleeve 468.

Refer now to FIG. 14, which shows a guidewire 410 having a tip construction similar to that shown in FIG. 13, wherein like reference numerals indicate similar structure. The core wire 413 in the embodiment of FIG. 13, however, has a tip portion 434 including one constant diameter portion 450, and one tapered portion 442, and the coiled ribbon 458 is attached around a portion of the tapered portion 442. The other aspects and components of the embodiment shown in FIG. 14 can include the same general structure and materials as discussed above with regard to FIG. 13.

In some specific embodiments, the guidewire 413 has the general structure set fourth in FIG. 14, wherein the core wire 413 is a distal portion of a core wire made of linear elastic nickel-titanium alloy, wherein the constant diameter portion 450 is about 0.0097 inches in diameter, and the tapered portion 442 is about 3 inches long, ending at the distal end thereof at a diameter of about 0.003 inches. The coil 458 is about 1.5 inches long, is made of flattened stainless steel wire having width and thickness dimensions of about 0.005 inches by about 0.001 inches. The coil 458 has a diameter that is tapered from about 0.0097 inches on its proximal end to about 0.003 inches on its distal end, and is attached to the core wire 413 at attachment points 464 and 465 using solder. The coil 458 overlaps the core wire 413 for about 1.1 inches, and extends distally of the core wire 413 for about 0.4 inches. The pitch of the coil portion that overlaps the core wire is about 0.04 inches and the pitch of the coil portion that extends distally of the core wire is about 0.08 inches. In some such embodiments, the portion of the guidewire where the coil 458 overlaps the core wire 413 for about 1.1 inches is plated, for example, with tin plating. The sleeve 468 is a polyurethane sleeve attached about the core wire 413 and coil 458. A hydrophilic coating is then coated onto the sleeve 468.

Refer now to FIG. 15, which shows a guidewire 410 having a tip construction similar to that shown in FIG. 13, wherein like reference numerals indicate similar structure. The core wire 413 in the embodiment of FIG. 15, however, has a tip portion 434 including two constant diameter portions 450, and 454, and one tapered portion 442. The coil 458 is attached around the constant diameter portion 454. In FIG. 15, the coil 458 is attached at two attachment points 464 and 465 about the constant diameter portion 454, is not tapered, and does not include a substantial pitch change along the length of the coil 458. The other aspects and components of the embodiment shown in FIG. 15 can include the same general structure and materials as discussed above with regard to FIG. 13.

Refer now to FIG. 16, which shows a guidewire 410 having a tip construction similar to that shown in FIG. 15, wherein like reference numerals indicate similar structure. In the embodiment of FIG. 16, however, the pitch of the coil 458 is lengthened distal to the attachment point 464 as compared to the pitch of the coil 458 proximal to the attachment point 464. The other aspects and components of the embodiment shown in FIG. 16 can include the same general structure and materials as discussed above with regard to FIG. 13.

Refer now to FIG. 17, which shows a guidewire 410 having a tip construction similar to that shown in FIG. 16, wherein like reference numerals indicate similar structure. In the embodiment of FIG. 17, however, only attachment point 464 near the distal end of the core wire 413 is used. The other aspects and components of the embodiment shown in FIG. 17 can include the same general structure and materials as discussed above with regard to FIG. 13.

Refer now to FIG. 18, which shows a guidewire 410 having a tip construction similar to that shown in FIG. 16, wherein like reference numerals indicate similar structure. In the embodiment of FIG. 18, however, only the more proximal attachment point 465 is used. The other aspects and components of the embodiment shown in FIG. 18 can include the same general structure and materials as discussed above with regard to FIG. 13.

Refer now to FIG. 19, which shows a guidewire 410 having a tip construction similar to that shown in FIG. 16, wherein like reference numerals indicate similar structure. In the embodiment of FIG. 19, however, the safety and/or shaping structure 458 has a coiled portion 490 that is coiled around the constant diameter portion 454, and then transforms into a non-coiled portion 492 that extends distally from the distal end of the core wire 413. The other aspects and components of the embodiment shown in FIG. 18 can include the same general structure and materials as discussed above with regard to FIG. 13.

Refer now to FIG. 20, which shows a guidewire 410 having a tip construction similar to that shown in FIG. 19, wherein like reference numerals indicate similar structure. In the embodiment of FIG. 20, however, the safety and/or shaping structure 458 includes two separate portions—a generally straight portion 492 that overlaps with the constant diameter portion 454 and extends distally from the distal end of the core wire 413, and a coiled portion 490 that is coiled around both the straight ribbon portion 492 and the constant diameter portion 454 to attach the straight portion 492 to the constant diameter portion 454. The other aspects and components of the embodiment shown in FIG. 18 can include the same general structure and materials as discussed above with regard to FIG. 13.

Refer now to FIG. 21, which is a partial cross sectional view of a guidewire 410 tip construction similar to that shown in FIG. 19, wherein like reference numerals indicate similar structure. Like the embodiment of FIG. 19, the embodiment shown in FIG. 21 includes a safety and/or shaping structure 458 that has a coiled portion 490 that is coiled around the constant diameter portion 454, and then safety and/or shaping structure 458 transforms into a non-coiled portion 492 that extends distally from the distal end of the core wire 413. However, in FIG. 21, the non-coiled portion 492 is twisted to form a helix shaped wire. The other aspects and components of the embodiment shown in FIG. 21 can include the same general structure and materials as discussed above with regard to FIG. 13.

Refer now to FIG. 22, which is a partial cross sectional view of a guidewire 410 including a tip construction similar to the distal tip portion 230 of the guidewire 210 shown in FIGS. 9 and 10, wherein like reference numerals indicate similar structure. In the embodiment of FIG. 22, however, the tip construction includes a coiled safety and/or shaping structure 458 rather than a non-coiled ribbon 258 as shown of FIGS. 9 and 10. The coil is attached to the guidewire at two attachment points 464 and 465, for example, through soldering. The other aspects and components of the embodiment shown in FIG. 21 can include the same general structure and materials as discussed above with regard to FIGS. 9 and 10, and/or with regard to FIG. 13.

Figure 23:
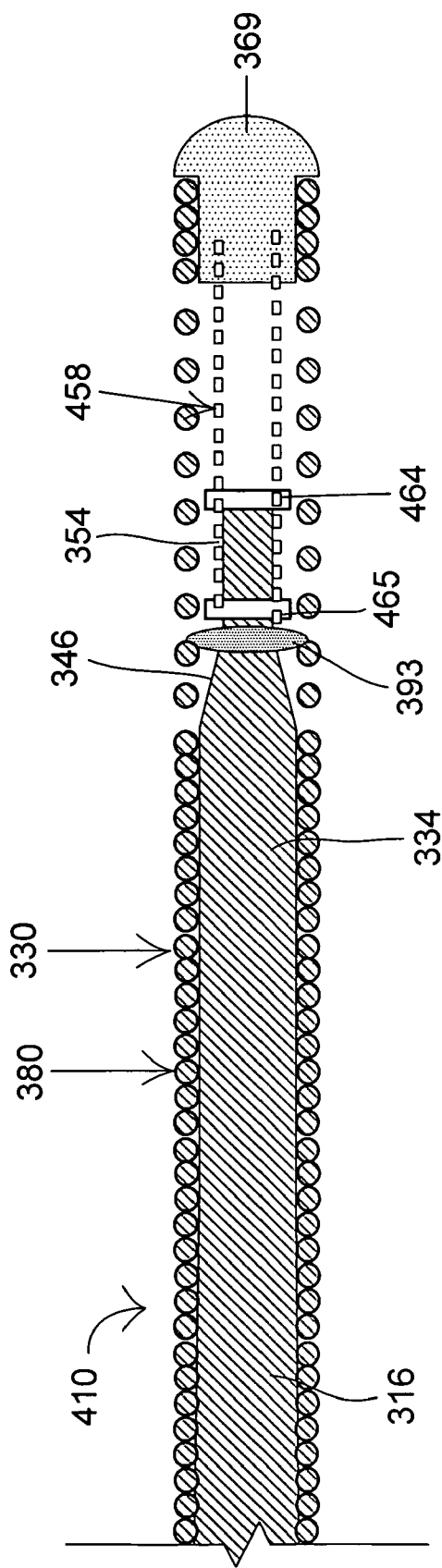
FIG. 23 is a cross sectional fragmentary view of another embodiment of a guidewire including another alternative tip construction.

Refer now to FIG. 23, which is a partial cross sectional view of a guidewire 410 including a tip construction similar to the distal tip portion 230 of the guidewire 210 shown in FIGS. 11 and 12, wherein like reference numerals indicate similar structure. In the embodiment of FIG. 23, however, the tip construction includes a coiled safety and/or shaping structure 458 rather than a non-coiled structure 258 as shown of FIGS. 11 and 12. The coil is attached to the guidewire at two attachment points 464 and 465, for example, through soldering. Additionally, the embodiment of FIG. 21 also does not include an inner coil 390 and a spacer 395 as shown in FIGS. 11 and 12. The other aspects and components of the embodiment shown in FIG. 21 can include the same general structure and materials as discussed above with regard to FIGS. 11 and 12, and/or with regard to FIG. 13.

It should be understood that this disclosure is, in many respects, only illustrative. Changes may be made in details, particularly in matters of shape, size, and arrangement of steps without exceeding the scope of the invention. For example, alternative structure can be used in connecting the proximal and distal sections of guidewires. Additionally, alternative tip constructions including a flexible coil tip, a polymer jacket tip, a tip including a coiled safety/shaping wire, or combination thereof, and other such structure may be placed on the guidewire. The invention's scope is, of course, defined in the language in which the appended claims are expressed.

What is claimed is:

1. A guidewire, comprising:
  a proximal section having a distal end, wherein the distal end of the proximal section includes a flexibility transition region;
  a distal section comprising a linear-elastic nickel-titanium alloy, the distal section having a proximal end, wherein the proximal end of the distal section includes a flexibility transition region;
  a connector comprising a metal alloy having a Unified Numbering System (UNS) designation of N06625 or N10276, or a nickel-molybdenum alloy designated B-2, the connector being disposed adjacent the distal end of the proximal section and the proximal end of the distal section, the connector adapted and configured for joining the proximal section to the distal section and is welded to at least the distal section; and
  a polymer sleeve disposed about a portion of the distal section.

2. A guidewire of claim 1, wherein the guidewire further includes a coil disposed about a portion of the distal section, the coil having a distal portion that extends distally of the distal section.

3. A guidewire, comprising:
  a proximal section comprising a metal or metal alloy, the proximal section having a distal end;
  a distal section comprising a linear elastic nickel-titanium alloy, the distal section having a proximal end; and a connector disposed adjacent the distal end of the proximal section and the proximal end of the distal section, the connector comprising a metal alloy having a Unified Numbering System (UNS) designation of N06625, the connector being adapted and configured for permanently joining the proximal section and the distal section.

4. A guidewire as in claim 3, wherein the proximal section has a first flexibility and the distal section has a second flexibility, and wherein the distal end of the proximal section and the proximal end of the distal section overlap to define a region that blends the first flexibility with the second flexibility.

5. A guidewire as in claim 3, wherein the distal end of the proximal section has a reduced size, and the proximal end of the distal section has a reduced size.

6. A guidewire as in claim 5, wherein the reduced size portions have a uniform profile.

7. A guidewire as in claim 5, wherein the reduced size portions have at least one of a taper or an interlocking shape.

8. A guidewire as in claim 3, wherein the distal end of the proximal section and the proximal end of the distal section are joined to define a butt joint.

9. A guidewire as in claim 3, wherein the distal end of the proximal section defines a tapered portion and the proximal end of the distal section defines a tapered portion, and the tapered portions at least partially overlap each other.

10. A guidewire as in claim 9, wherein the connector comprises connector material disposed between the tapered portions.

11. A guidewire as in claim 3, wherein the connector is welded to the proximal section.

12. A guidewire as in claim 11, wherein the metal or metal alloy of the proximal section comprises stainless steel, nickel-titanium alloy, nickel-chromium alloy, nickel-chromium-iron alloy, cobalt alloy, or combinations thereof.

13. A guidewire as in claim 12, wherein the proximal section comprises stainless steel.

14. A guidewire as in claim 3, wherein the guidewire further includes an outer structure disposed about at least a portion of the distal section.

15. A guidewire of claim 14, wherein the outer structure comprises a first coil disposed about a portion of the distal section.

16. A guidewire of claim 3, wherein the connector is welded to the distal section.

17. A guidewire as in claim 3, wherein the connector comprises a tubular member disposed about the distal end of the proximal section and the proximal end of the distal section.

18. A guidewire, comprising:
a proximal section having a distal end, wherein the distal end of the proximal section includes a flexibility transition region;
a distal section comprising a linear-elastic nickel-titanium alloy, the distal section having a proximal end, wherein to proximal end of the distal section includes a flexibility transition region;
a connector comprising a metal alloy having a Unified Numbering System (UNS) designation of N06625 or N10276, or a nickel-molybdenum alloy designated B-2, the connector being disposed adjacent the distal end of the proximal section and the proximal end of the distal section, the connector adapted and configured for joining to proximal section to the distal section and is welded to at least the distal section; and
a first coil disposed about a portion of the distal section.

19. A guidewire of claim 18, wherein the guidewire further includes an inner coil disposed about a portion of the distal section at least partially within the first coil, the inner coil having a distal portion that extends distally of the distal section.

20. The guidewire of claim 19, wherein the inner coil is adapted and configured to be a safety structure.

21. A guidewire, comprising:
a proximal section comprising a metal or metal alloy, the proximal section having a distal end;
a distal section comprising a linear elastic nickel-titanium alloy, the distal section having a proximal end;
a connector disposed adjacent the distal end of the proximal section and the proximal end of the distal section, the connector comprising a nickel-chromium alloy, a nickel-molybdenum alloy, or a cobalt alloy, the connector being adapted and configured for permanently joining the proximal section and the distal section; and
an outer structure disposed about at least a portion of the distal section, wherein the outer structure comprises a polymer sleeve.

22. A guidewire as in claim 21 wherein the guidewire further includes a flat ribbon attached to the distal section.

23. A guidewire of claim 21, wherein the guidewire further comprises a coil disposed about a portion of the distal section, the coil having a distal portion that extends distally of the distal section.

24. A guidewire, comprising:
a proximal section comprising a metal or metal alloy, the proximal section having a distal end;
a distal section comprising a linear elastic nickel-titanium alloy, the distal section having a proximal end;
a connector disposed adjacent the distal end of the proximal section and the proximal end of the distal section, the connector comprising a nickel-chromium alloy, a nickel-molybdenum alloy, or a cobalt alloy, the connector being adapted and configured for permanently joining the proximal section and the distal section;
an outer structure disposed about at least a portion of the distal section, wherein the outer structure comprises a first coil disposed about a portion of the distal section; and
an inner coil disposed about a portion of the distal section at least partially within the first coil, the inner coil having a distal portion that extends distally of the distal section.

25. The guidewire of claim 24, wherein the inner coil is adapted and configured to be a safety structure.

26. A guidewire, comprising:
a proximal section comprising a metal or metal alloy, the proximal section having a distal end;
a distal section comprising a linear elastic nickel-titanium alloy, the distal section having a proximal end;
a connector disposed adjacent the distal end of the proximal section and the proximal end of the distal section, the connector comprising a nickel-chromium alloy, a nickel-molybdenum alloy, or a cobalt alloy, the connector being adapted and configured for permanently joining the proximal section and the distal section;
an outer structure disposed about at least a portion of the distal section, wherein the outer structure comprises a first coil disposed about a portion of the distal section, and
a flat ribbon attached to the distal section.

27. A guidewire, comprising:
a proximal section comprising a metal or metal alloy, the proximal section having a distal end;

a distal section comprising a linear elastic nickel-titanium alloy, the distal section having a proximal end; and a connector disposed adjacent the distal end of the proximal section and the proximal end of the distal section, wherein the connector comprises a metal alloy having a Unified Numbering System (UNS) designation of N10276, the connector being adapted and configured for permanently joining the proximal section and the distal section.

28. A guidewire, comprising:

a proximal section comprising a metal or metal alloy, the proximal section having a distal end;

a distal section comprising a linear elastic nickel-titanium alloy, the distal section having a proximal end; and a connector disposed adjacent the distal end of the proximal section and the proximal end of the distal section, wherein the connector comprises a nickel-molybdenum alloy designated B-2, the connector being adapted and configured for permanently joining the proximal section and the distal section.

29. A guidewire, comprising:

a proximal section having a distal end, wherein the distal end of the proximal section includes a flexibility transition region;

a distal section comprising a linear-elastic nickel-titanium alloy, the distal section having a proximal end, wherein the proximal end of the distal section includes a flexibility transition region; and a connector comprising a metal alloy having a Unified Numbering System (UNS) designation of N06625 or N10276, or a nickel-molybdenum alloy designated B-2, the connector being disposed adjacent the distal end of the proximal section and the proximal end of the distal section, the connector adapted and configured for joining the proximal section to the distal section and is welded to at least the distal section.

30. A guidewire as in claim 29, wherein the proximal section has a first flexibility and the distal section has a second flexibility, and wherein flexibility transition regions overlap to define a region that blends the first flexibility with the second flexibility.

31. A guidewire as in claim 29, wherein the proximal section comprises stainless steel.

32. A guidewire as in claim 29, wherein the connector comprises a tubular member.

33. A guidewire as in claim 29, wherein at least a portion of the connector is disposed between the flexibility transition regions.

34. A method of manufacturing a guidewire, comprising the steps of:

providing a proximal section having a distal end;

providing a distal section comprising a linear elastic nickel-titanium alloy, the distal section having a proximal end;

forming flexibility transition regions in the distal end of the proximal section and the proximal end of the distal section; and connecting the distal end of the proximal section and the proximal end of the distal section using a connector, the connector comprising a nickel-chromium alloy, a nickel-molybdenum alloy, or a cobalt alloy, wherein the connector is welded to the distal section, and wherein the connector is adapted and configured for permanently joining the proximal section to the distal section;

wherein the step of connecting the distal end of the proximal section and the proximal end of the distal section includes overlapping the proximal and distal ends.

35. A guidewire, comprising:

a core wire having a proximal section having a distal end, and a distal section having a proximal end and a distal end, the distal section including a linear elastic nickel-titanium alloy;

a connector disposed adjacent the distal end of the proximal section and the proximal end of the distal section, the connector joining the proximal section to the distal section, the connector comprising a nickel-chromium alloy, a nickel-molybdenum alloy, or a cobalt alloy, the connector being welded to at least the distal section;

an inner coil having a proximal region and a distal region, the proximal region of the coil connected to the distal end of the distal section, and the distal region of the coil extending distally beyond the distal end of the distal section; and an outer structure disposed about at least a portion of the distal section and the inner coil.

36. A guidewire as in claim 35, wherein the outer structure is a polymer sheath.

37. A guidewire as in claim 36, wherein the polymer sheath extends distally beyond the distal region of the coil to form a tip.

38. A guidewire of claim 35, wherein the outer structure is an outer coil.

39. A guidewire as in claim 35, wherein the inner coil is a flat wire coil.

* * * * *